United States Patent
Perryman et al.

(10) Patent No.: US 12,151,107 B2
(45) Date of Patent: Nov. 26, 2024

(54) SYSTEMS AND METHODS TO SENSE STIMULATION ELECTRODE TISSUE IMPEDANCE

(71) Applicant: Curonix LLC, Pompano Beach, FL (US)

(72) Inventors: Laura Tyler Perryman, Pompano Beach, FL (US); Patrick Larson, Surfside, FL (US); Richard LeBaron, Miami Beach, FL (US)

(73) Assignee: CURONIX LLC, Pompano Beach, FL (US)

( * ) Notice: Subject to any disclaimer, the term of this patent is extended or adjusted under 35 U.S.C. 154(b) by 194 days.

(21) Appl. No.: 17/665,857

(22) Filed: Feb. 7, 2022

(65) Prior Publication Data
US 2022/0152388 A1 May 19, 2022

Related U.S. Application Data

(63) Continuation of application No. 16/265,669, filed on Feb. 1, 2019, now abandoned.
(Continued)

(51) Int. Cl.
*A61N 1/36* (2006.01)
*A61N 1/08* (2006.01)
(Continued)

(52) U.S. Cl.
CPC ............. *A61N 1/3614* (2017.08); *A61N 1/08* (2013.01); *A61N 1/36125* (2013.01);
(Continued)

(58) Field of Classification Search
CPC .. A61N 1/08; A61N 1/36075; A61N 1/36125; A61N 1/3614; A61N 1/36171;
(Continued)

(56) References Cited

U.S. PATENT DOCUMENTS

| 2,990,547 A | 6/1961 | McDougal |
| 3,662,758 A | 5/1972 | Glover |

(Continued)

FOREIGN PATENT DOCUMENTS

| CN | 1678370 | 10/2005 |
| CN | 101185789 | 5/2008 |

(Continued)

OTHER PUBLICATIONS

US 5,197,469 A, 03/1993, Adams (withdrawn)
(Continued)

*Primary Examiner* — Scott Luan
(74) *Attorney, Agent, or Firm* — Maschoff Brennan

(57) ABSTRACT

A method includes: transmitting a first set of radio-frequency (RF) pulses to an implantable wireless stimulator device such that electric currents are created from the first set of RF pulses and flown through a calibrated internal load on the implantable wireless stimulator device; in response to the electric currents flown through a calibrated internal load, recording a first set of RF reflection measurements; transmitting a second set of radio-frequency (RF) pulses to the implantable wireless stimulator device such that stimulation currents are created from the second set of RF pulses and flown through an electrode of the implantable wireless stimulator device to tissue surrounding the electrode; in response to the stimulation currents flown through the electrode to the surrounding tissue, recording a second set of RF reflection measurements; and characterizing an electrode-tissue impedance by comparing the second set of RF reflection measurements with the first set of RF reflections measurements.

20 Claims, 9 Drawing Sheets

Related U.S. Application Data

(60) Provisional application No. 62/624,982, filed on Feb. 1, 2018.

(51) Int. Cl.
*A61N 1/372* (2006.01)
*A61N 1/378* (2006.01)

(52) U.S. Cl.
CPC ..... *A61N 1/36171* (2013.01); *A61N 1/36175* (2013.01); *A61N 1/37223* (2013.01); *A61N 1/3787* (2013.01); *A61N 1/36075* (2013.01)

(58) Field of Classification Search
CPC ............ A61N 1/36175; A61N 1/37223; A61N 1/3787
See application file for complete search history.

(56) References Cited

U.S. PATENT DOCUMENTS

| | | | |
|---|---|---|---|
| 3,663,758 A | 5/1972 | Erbert |
| 3,727,616 A | 4/1973 | Lenzkes |
| 4,057,069 A | 11/1977 | Dorffer et al. |
| 4,102,344 A | 7/1978 | Conway et al. |
| 4,223,679 A | 9/1980 | Schulman et al. |
| 4,494,950 A | 1/1985 | Fischell |
| 4,524,774 A | 6/1985 | Hildebrandt |
| 4,525,774 A | 6/1985 | Kino et al. |
| 4,532,930 A | 8/1985 | Crosby |
| 4,561,443 A | 12/1985 | Hogrefe et al. |
| 4,592,359 A | 6/1986 | Galbraith |
| 4,612,934 A | 9/1986 | Borkan |
| 4,628,933 A | 12/1986 | Michelson |
| 4,665,896 A | 5/1987 | LaForge |
| 4,726,378 A | 2/1988 | Kaplan |
| 4,736,747 A | 4/1988 | Drake |
| 4,736,752 A | 4/1988 | Munck |
| 4,741,339 A | 5/1988 | Harrison et al. |
| 4,750,499 A | 6/1988 | Hoffer |
| 4,793,353 A | 12/1988 | Borkan |
| 4,837,049 A | 6/1989 | Byers et al. |
| 4,926,879 A | 5/1990 | Sevrain |
| 4,947,844 A | 8/1990 | McDermott |
| 5,058,581 A | 10/1991 | Silvian |
| 5,070,535 A | 12/1991 | Hochmair et al. |
| 5,193,539 A | 3/1993 | Schulman et al. |
| 5,262,793 A | 11/1993 | Sperry |
| 5,314,458 A | 5/1994 | Najafi et al. |
| 5,343,766 A | 9/1994 | Lee |
| 5,358,514 A | 10/1994 | Schulman et al. |
| 5,411,535 A | 5/1995 | Fujii et al. |
| 5,583,510 A | 12/1996 | Ponnapalli et al. |
| 5,591,217 A | 1/1997 | Barreras |
| 5,626,630 A | 5/1997 | Markowitz et al. |
| 5,735,887 A | 4/1998 | Barreras, Sr. et al. |
| 5,769,877 A | 6/1998 | Barreras |
| 5,861,019 A | 1/1999 | Sun et al. |
| 5,991,664 A | 11/1999 | Seligman |
| 5,995,874 A | 11/1999 | Borza |
| 6,141,588 A | 10/2000 | Cox et al. |
| 6,164,284 A | 12/2000 | Shulman et al. |
| 6,175,752 B1 | 1/2001 | Say et al. |
| 6,321,118 B1 | 11/2001 | Hahn |
| 6,364,889 B1 | 4/2002 | Kheiri et al. |
| 6,415,184 B1 | 7/2002 | Ishikawa et al. |
| 6,445,953 B1 | 9/2002 | Bulkes et al. |
| 6,445,955 B1 | 9/2002 | Michelson et al. |
| 6,458,157 B1 | 10/2002 | Suaning |
| 6,463,336 B1 | 10/2002 | Mawhinney |
| 6,516,227 B1 | 2/2003 | Meadows et al. |
| 6,564,807 B1 | 5/2003 | Schulman et al. |
| 6,611,715 B1 | 8/2003 | Boveja |
| 6,615,081 B1 | 9/2003 | Boveja |
| 6,647,296 B2 | 11/2003 | Fischell et al. |
| 6,662,052 B1 | 12/2003 | Sarwal et al. |
| 6,684,104 B2 | 1/2004 | Gordon et al. |
| 6,690,974 B2 | 2/2004 | Archer et al. |
| 6,889,086 B2 | 5/2005 | Mass et al. |
| 6,895,280 B2 | 5/2005 | Meadows et al. |
| 6,972,727 B1 | 12/2005 | West et al. |
| 7,003,350 B2 | 2/2006 | Denker et al. |
| 7,027,874 B1 | 4/2006 | Sawan et al. |
| 7,110,823 B2 | 9/2006 | Whitehurst et al. |
| 7,177,690 B2 | 2/2007 | Woods et al. |
| 7,214,189 B2 | 5/2007 | Zdeblick |
| 7,277,728 B1 | 10/2007 | Kauhanen |
| 7,283,875 B2 | 10/2007 | Larsson |
| 7,317,947 B2 | 1/2008 | Wahlstrand et al. |
| 7,436,752 B2 | 10/2008 | He |
| 7,450,992 B1 | 11/2008 | Cameron |
| 7,471,257 B2 | 12/2008 | Candal et al. |
| 7,489,248 B2 | 2/2009 | Gengel et al. |
| 7,616,991 B2 | 11/2009 | Mann et al. |
| 7,620,451 B2 | 11/2009 | Demarais |
| 7,630,771 B2 | 12/2009 | Cauller |
| 7,664,552 B2 | 2/2010 | Wahlstrand et al. |
| 7,729,781 B2 | 6/2010 | Swoyer et al. |
| 7,738,963 B2 | 6/2010 | Hickman et al. |
| 7,738,964 B2 | 6/2010 | Von Arx et al. |
| 7,765,013 B2 | 7/2010 | Blick et al. |
| 7,853,333 B2 | 12/2010 | Demarais |
| 7,869,885 B2 | 1/2011 | Begnaud et al. |
| 7,894,905 B2 | 2/2011 | Pless et al. |
| 7,904,170 B2 | 3/2011 | Harding |
| 7,908,014 B2 | 3/2011 | Schulman et al. |
| 7,917,226 B2 | 3/2011 | Nghiem et al. |
| 7,939,346 B2 | 5/2011 | Blick et al. |
| 8,170,672 B2 | 5/2012 | Weiss et al. |
| 8,242,968 B2 | 8/2012 | Conrad et al. |
| 8,320,850 B1 | 11/2012 | Khlat |
| 8,332,040 B1 | 12/2012 | Winstrom |
| 8,634,928 B1 | 1/2014 | O'Drisco et al. |
| D714,288 S | 9/2014 | Aumiller et al. |
| 8,847,548 B2 | 9/2014 | Kesler et al. |
| 8,849,412 B2 | 9/2014 | Perryman et al. |
| 8,903,502 B2 | 12/2014 | Perryman |
| D721,701 S | 1/2015 | Al-Nasser |
| D725,071 S | 3/2015 | Lee et al. |
| D725,072 S | 3/2015 | Kim et al. |
| D725,652 S | 3/2015 | Ishii |
| D734,330 S | 7/2015 | Huang et al. |
| 9,220,897 B2 | 12/2015 | Perryman et al. |
| 9,242,103 B2 | 1/2016 | Perryman et al. |
| 9,254,393 B2 | 2/2016 | Perryman et al. |
| 9,409,030 B2 | 8/2016 | Perryman et al. |
| 9,446,255 B2 | 9/2016 | Towe et al. |
| 9,566,449 B2 | 2/2017 | Perryman et al. |
| 9,757,571 B2 | 9/2017 | Perryman |
| 9,789,314 B2 | 10/2017 | Perryman |
| 9,974,965 B2 | 5/2018 | Andresen et al. |
| 10,238,874 B2 | 3/2019 | Perryman |
| 10,293,169 B2 | 5/2019 | Perryman et al. |
| 10,315,039 B2 | 6/2019 | Perryman et al. |
| 10,420,947 B2 | 9/2019 | Larson et al. |
| 10,471,262 B2 | 11/2019 | Perryman et al. |
| 10,953,228 B2 | 3/2021 | Perryman et al. |
| 2001/0010662 A1 | 8/2001 | Saitou et al. |
| 2002/0058972 A1 | 5/2002 | Minogue et al. |
| 2002/0082668 A1 | 6/2002 | Ingman |
| 2002/0091420 A1 | 7/2002 | Minogue et al. |
| 2002/0095195 A1 | 7/2002 | Mass |
| 2002/0103513 A1 | 8/2002 | Minogue et al. |
| 2002/0123779 A1 | 9/2002 | Von Arx et al. |
| 2002/0128686 A1 | 9/2002 | Minogue et al. |
| 2002/0128693 A1 | 9/2002 | Minogue et al. |
| 2002/0133195 A1 | 9/2002 | Minogue et al. |
| 2003/0078633 A1 | 4/2003 | Firlik et al. |
| 2003/0114898 A1 | 6/2003 | Von Arx et al. |
| 2003/0114899 A1 | 6/2003 | Woods et al. |
| 2003/0139782 A1 | 7/2003 | Duncan et al. |
| 2003/0169207 A1 | 9/2003 | Beigel |
| 2003/0204224 A1 | 10/2003 | Torgerson et al. |
| 2004/0044385 A1 | 3/2004 | Fenn et al. |
| 2004/0059392 A1 | 3/2004 | Parramon et al. |

(56) References Cited

U.S. PATENT DOCUMENTS

| | | |
|---|---|---|
| 2004/0082979 A1 | 4/2004 | Tong et al. |
| 2004/0127942 A1 | 7/2004 | Yomtov et al. |
| 2004/0138723 A1 | 7/2004 | Malick et al. |
| 2004/0167587 A1 | 8/2004 | Thompson et al. |
| 2004/0176803 A1 | 9/2004 | Whelan et al. |
| 2004/0220621 A1 | 11/2004 | Zhou |
| 2004/0230263 A1 | 11/2004 | Samulski |
| 2004/0243208 A1 | 12/2004 | Jordan |
| 2005/0027207 A1 | 2/2005 | Westbrook et al. |
| 2005/0119716 A1 | 6/2005 | McClure et al. |
| 2005/0137668 A1 | 6/2005 | Khan |
| 2005/0245994 A1 | 11/2005 | Varrichio et al. |
| 2006/0001583 A1 | 1/2006 | Bisig |
| 2006/0003721 A1 | 1/2006 | Bisig |
| 2006/0047327 A1 | 3/2006 | Colvin et al. |
| 2006/0085039 A1 | 4/2006 | Hastings et al. |
| 2006/0085042 A1 | 4/2006 | Hastings et al. |
| 2006/0149331 A1 | 7/2006 | Man et al. |
| 2006/0161216 A1 | 7/2006 | Constance |
| 2006/0161225 A1 | 7/2006 | Sormann et al. |
| 2006/0178718 A1 | 8/2006 | Jordan |
| 2006/0206168 A1 | 9/2006 | Minogue et al. |
| 2006/0287686 A1 | 12/2006 | Cullen et al. |
| 2006/0289528 A1 | 12/2006 | Chiu et al. |
| 2007/0055322 A1 | 3/2007 | Forsberg et al. |
| 2007/0055324 A1 | 3/2007 | Thompson et al. |
| 2007/0066995 A1 | 3/2007 | Strother et al. |
| 2007/0100385 A1 | 5/2007 | Rawat |
| 2007/0100395 A1 | 5/2007 | Ibrahim |
| 2007/0100935 A1 | 5/2007 | Miyazaki et al. |
| 2007/0106337 A1 | 5/2007 | Errico et al. |
| 2007/0109208 A1 | 5/2007 | Turner |
| 2007/0112402 A1 | 5/2007 | Grill et al. |
| 2007/0123948 A1 | 5/2007 | Dal Molin |
| 2007/0156179 A1 | 7/2007 | S.E. |
| 2007/0208394 A1 | 9/2007 | King et al. |
| 2007/0213773 A1 | 9/2007 | Hill et al. |
| 2007/0213783 A1 | 9/2007 | Pless |
| 2007/0239224 A1 | 10/2007 | Bennett et al. |
| 2007/0254632 A1 | 11/2007 | Beadle et al. |
| 2007/0255223 A1 | 11/2007 | Phillips et al. |
| 2007/0255373 A1 | 11/2007 | Metzler et al. |
| 2007/0257636 A1 | 11/2007 | Phillips et al. |
| 2007/0265543 A1 | 11/2007 | VanSickle et al. |
| 2007/0265690 A1 | 11/2007 | Lichtenstein et al. |
| 2007/0288066 A1 | 12/2007 | Christman et al. |
| 2007/0293909 A1 | 12/2007 | Cowan et al. |
| 2008/0010358 A1 | 1/2008 | Jin |
| 2008/0046012 A1 | 2/2008 | Covalin et al. |
| 2008/0077184 A1 | 3/2008 | Denker et al. |
| 2008/0077188 A1 | 3/2008 | Denker et al. |
| 2008/0077189 A1 | 3/2008 | Ostroff |
| 2008/0103558 A1 | 5/2008 | Wenzel |
| 2008/0154217 A1 | 6/2008 | Carrez et al. |
| 2008/0161883 A1 | 7/2008 | Conor |
| 2008/0266123 A1 | 10/2008 | Ales et al. |
| 2008/0279896 A1 | 11/2008 | Heinen et al. |
| 2008/0281244 A1 | 11/2008 | Jacobs |
| 2009/0018599 A1 | 1/2009 | Hastings et al. |
| 2009/0099405 A1 | 4/2009 | Schneider et al. |
| 2009/0105784 A1 | 4/2009 | Massoud-Ansari |
| 2009/0105795 A1 | 4/2009 | Minogue et al. |
| 2009/0125091 A1 | 5/2009 | Schoenbach et al. |
| 2009/0132002 A1 | 5/2009 | Kieval |
| 2009/0132003 A1 | 5/2009 | Borgens et al. |
| 2009/0200985 A1 | 8/2009 | Zane et al. |
| 2009/0204170 A1 | 8/2009 | Hastings et al. |
| 2009/0234407 A1 | 9/2009 | Hastings et al. |
| 2009/0248112 A1 | 10/2009 | Mumbru et al. |
| 2009/0251101 A1 | 10/2009 | Phillips et al. |
| 2009/0270948 A1 | 10/2009 | Nghiem et al. |
| 2009/0270951 A1 | 10/2009 | Kallmyer |
| 2009/0292339 A1 | 11/2009 | Erickson |
| 2010/0010565 A1 | 1/2010 | Lichtenstein et al. |
| 2010/0053789 A1 | 3/2010 | Duric et al. |
| 2010/0114143 A1 | 5/2010 | Albrecht et al. |
| 2010/0114198 A1 | 5/2010 | Donofrio et al. |
| 2010/0125269 A1 | 5/2010 | Emmons et al. |
| 2010/0125312 A1 | 5/2010 | Stevenson et al. |
| 2010/0137938 A1 | 6/2010 | Kishawi et al. |
| 2010/0168818 A1 | 7/2010 | Barror et al. |
| 2010/0174340 A1 | 7/2010 | Simon |
| 2010/0179449 A1 | 7/2010 | Chow et al. |
| 2010/0198039 A1 | 8/2010 | Towe |
| 2010/0198307 A1 | 8/2010 | Toy et al. |
| 2010/0231382 A1 | 9/2010 | Tayrani et al. |
| 2010/0234919 A1 | 9/2010 | Minogue et al. |
| 2010/0234922 A1 | 9/2010 | Forsell |
| 2010/0241051 A1 | 9/2010 | Dacey, Jr. et al. |
| 2010/0268298 A1 | 10/2010 | Moffitt et al. |
| 2010/0269339 A1 | 10/2010 | Dye et al. |
| 2010/0298742 A1 | 11/2010 | Perlman et al. |
| 2010/0331934 A1 | 12/2010 | McDonald et al. |
| 2011/0021887 A1 | 1/2011 | Crivelli et al. |
| 2011/0029043 A1 | 2/2011 | Frysz et al. |
| 2011/0040350 A1 | 2/2011 | Griffith |
| 2011/0054563 A1 | 3/2011 | Janzig et al. |
| 2011/0074342 A1 | 3/2011 | MacLaughlin |
| 2011/0077698 A1 | 3/2011 | Tsampazis et al. |
| 2011/0098583 A1 | 4/2011 | Pandia et al. |
| 2011/0106220 A1 | 5/2011 | DeGiorgio et al. |
| 2011/0120822 A1 | 5/2011 | Kondou et al. |
| 2011/0121822 A1 | 5/2011 | Parsche |
| 2011/0125214 A1 | 5/2011 | Goetz et al. |
| 2011/0130804 A1 | 6/2011 | Lin et al. |
| 2011/0144468 A1 | 6/2011 | Boggs et al. |
| 2011/0152750 A1 | 6/2011 | Dacey, Jr. et al. |
| 2011/0166630 A1 | 7/2011 | Phillips et al. |
| 2011/0172733 A1 | 7/2011 | Lima et al. |
| 2011/0190849 A1 | 8/2011 | Faltys et al. |
| 2011/0208266 A1 | 8/2011 | Minogue et al. |
| 2011/0245892 A1 | 10/2011 | Kast et al. |
| 2011/0276108 A1 | 11/2011 | Crowe et al. |
| 2012/0004708 A1 | 1/2012 | Chen et al. |
| 2012/0004709 A1 | 1/2012 | Chen et al. |
| 2012/0095461 A1* | 4/2012 | Herscher ............ A61B 18/1492 606/45 |
| 2012/0116477 A1 | 5/2012 | Crowe et al. |
| 2012/0143282 A1 | 6/2012 | Fukui et al. |
| 2012/0158407 A1 | 6/2012 | Forsell |
| 2012/0194399 A1 | 8/2012 | Bily et al. |
| 2012/0215218 A1 | 8/2012 | Lipani |
| 2012/0239107 A1 | 9/2012 | Kallmyer |
| 2012/0283800 A1 | 11/2012 | Perryman et al. |
| 2012/0302821 A1 | 11/2012 | Burnett |
| 2012/0330384 A1 | 12/2012 | Perryman et al. |
| 2013/0016016 A1 | 1/2013 | Lin et al. |
| 2013/0066400 A1 | 3/2013 | Perryman et al. |
| 2013/0079849 A1 | 3/2013 | Perryman et al. |
| 2013/0131752 A1 | 5/2013 | Rawat |
| 2013/0018439 A1 | 6/2013 | Chow et al. |
| 2013/0165991 A1 | 6/2013 | Kim |
| 2013/0226212 A1 | 8/2013 | Stevenson et al. |
| 2013/0310901 A1 | 11/2013 | Perryman et al. |
| 2013/0320773 A1* | 12/2013 | Schatz .................... H02J 50/70 307/104 |
| 2014/0031837 A1 | 1/2014 | Perryman et al. |
| 2014/0047713 A1 | 2/2014 | Singh et al. |
| 2014/0058480 A1 | 2/2014 | Perryman et al. |
| 2014/0058481 A1 | 2/2014 | Perryman et al. |
| 2014/0169142 A1 | 6/2014 | Heck et al. |
| 2014/0266935 A1 | 9/2014 | Tankiewicz |
| 2014/0336727 A1 | 11/2014 | Perryman et al. |
| 2015/0182753 A1 | 7/2015 | Harris et al. |
| 2015/0297900 A1* | 10/2015 | Perryman ............ A61N 1/3787 607/60 |
| 2015/0321017 A1 | 11/2015 | Perryman et al. |
| 2016/0101287 A1 | 4/2016 | Perryman |
| 2016/0136438 A1 | 5/2016 | Perryman et al. |
| 2016/0136439 A1 | 5/2016 | Andresen et al. |
| 2016/0339258 A1 | 11/2016 | Perryman et al. |
| 2016/0361535 A1 | 12/2016 | Perryman et al. |
| 2016/0367825 A1 | 12/2016 | Perryman et al. |
| 2017/0036033 A9 | 2/2017 | Perryman et al. |

(56) References Cited

U.S. PATENT DOCUMENTS

| | | |
|---|---|---|
| 2017/0189683 A1 | 7/2017 | Perryman et al. |
| 2018/0008828 A1 | 1/2018 | Perryman |
| 2018/0169423 A1 | 6/2018 | Larson et al. |
| 2018/0236248 A1 | 8/2018 | Perryman |
| 2018/0264277 A1 | 9/2018 | Perryman |
| 2019/0229771 A1 | 7/2019 | Lee et al. |
| 2019/0232057 A1 | 8/2019 | Perryman et al. |
| 2019/0247660 A1 | 8/2019 | Perryman |
| 2019/0381327 A1 | 12/2019 | Perryman et al. |
| 2020/0016415 A1 | 1/2020 | Perryman et al. |
| 2020/0016416 A1 | 1/2020 | Perryman et al. |
| 2020/0222703 A1 | 7/2020 | Perryman et al. |
| 2021/0187311 A1 | 6/2021 | Perryman et al. |
| 2021/0275813 A1 | 9/2021 | Perryman et al. |
| 2022/0088398 A1 | 3/2022 | Perryman et al. |
| 2022/0126105 A1 | 4/2022 | Perryman et al. |

FOREIGN PATENT DOCUMENTS

| | | |
|---|---|---|
| CN | 101217320 | 7/2008 |
| CN | 101352596 | 1/2009 |
| CN | 101773701 | 7/2010 |
| CN | 101842131 | 9/2010 |
| CN | 201676401 | 12/2010 |
| CN | 102120060 | 7/2011 |
| EP | 2462981 | 6/2001 |
| EP | 1588609 | 10/2005 |
| EP | 2694154 | 1/2018 |
| EP | 3403690 | 8/2020 |
| ES | 2341347 | 6/2010 |
| JP | H10 509901 | 9/1998 |
| JP | 2002524124 | 8/2002 |
| JP | 2005531371 | 10/2005 |
| JP | 2008023353 | 2/2008 |
| JP | 2008161667 | 7/2008 |
| JP | 2008528222 | 7/2008 |
| JP | 2009523402 | 6/2009 |
| JP | 2010534114 | 11/2010 |
| JP | 201155912 | 3/2011 |
| JP | 2011510787 | 4/2011 |
| JP | 2012508624 | 4/2012 |
| WO | WO 9620754 | 7/1996 |
| WO | WO 2000/013585 | 3/2000 |
| WO | WO 2004/002572 | 1/2004 |
| WO | WO 2004/004826 | 1/2004 |
| WO | WO 2006/113802 | 10/2006 |
| WO | WO 2006/128037 | 11/2006 |
| WO | WO 2007/059386 | 5/2007 |
| WO | WO 2007/081971 | 7/2007 |
| WO | WO 2009/015005 | 1/2009 |
| WO | WO 2010/005746 | 1/2010 |
| WO | WO 2010/051189 | 5/2010 |
| WO | WO 2010/053789 | 5/2010 |
| WO | WO 2010/057046 | 5/2010 |
| WO | WO 2010/104569 | 9/2010 |
| WO | WO 2011/079309 | 6/2011 |
| WO | WO 2012/103519 | 8/2012 |
| WO | WO 2012/138782 | 10/2012 |
| WO | WO 2013/019757 | 2/2013 |
| WO | WO 2013/025632 | 2/2013 |
| WO | WO 2013/040549 | 3/2013 |
| WO | WO 2017/214638 | 12/2017 |

OTHER PUBLICATIONS

PCT International Preliminary Report on Patentability in International Appln. No. PCT/US2019/016395, dated Aug. 4, 2020, 7 pages.
PCT International Search Report and Written Opinion in International Appln. No. PCT/US2019/16395, dated Apr. 30, 2019, 9 pages.
Search Report in European Appln. No. 19746618.8, dated Sep. 14, 2021, 7 pages.
Stensaas et al., "Histopathological Evaluation of Materials Implanted in the Cerebral Cortex," Acta neuropath. (Berl.) 41,145-155, year 1978, 2 pages.
Turner et al., "Cerebral Astrocyte Response to Micromachined Silicon Implants," Experimental Neurology 156, 33-49, dated Oct. 30, 1998, 17 pages.
Weiland et al., "Chronic Neural Stimulation with Thin-Film, Iridium Oxide Electrodes," IEEE Transactions on Biomedic Engineering, vol. 47, Issue 7, dated Aug. 2000, 7 pages.
Williams et al., "Complex impedance spectroscopy for monitoring tissue responses to inserted neural implants," J. Neural Eng. 4, 410-423, dated Nov. 27, 2007, 14 pages.
U.S. Appl. No. 14/445,159, filed Nov. 13, 2014, Perryman et al.
U.S. Appl. No. 29/478,687, filed Jan. 7, 2003, Perryman et al.
CA Office Action in Canadian Appln. No. 2831138, dated Oct. 30, 2020, 4 pages.
CN OA in Chinese Appln. No. 201710675346.5, dated Jun. 1, 2020, 11 pages (with English translation).
EP European Search Report in European Appln. No. 12831083.6, dated Aug. 17, 2015, 9 pages.
EP European Search Report in European Appln. No. 17208566.4, dated Sep. 26, 2018, 10 pages.
EP Extended European Search Report in European Appln. No. 18150779.9, dated May 9, 2018, 7 pages.
EP Extended European Search Report in European Appln. No. 20209052.8, dated Apr. 14, 2021, 7 pages.
EP Office Action in European Appln. No. 12740011.7, dated Sep. 13, 2018, 5 pages.
European Search Report in European Appln. No. 12767575.9, dated Jan. 11, 2018, 6 pages.
European Search Report in European Appln. No. 19186209.3, dated Nov. 25, 2019, 8 pages.
Extended European Search report in Appln. No. 12740011.7, dated Sep. 9, 2015, 6 pages.
Extended European Search report in Appln. No. 12767575.9, dated Nov. 7, 2014, 7 pages.
Extended European Search Report in Appln. No. 1281083.6, dated Aug. 17, 2015, 9 pages.
Extended European Search report in Appln. No. 12819482.6, dated Apr. 28, 2015, 7 pages.
Extended European Search Report in Appln. No. 12824347.4, dated Apr. 22, 2015, 6 pages.
Extended European Search Report in Appln. No. 15793285.6, dated Dec. 12, 2017, 7 pages.
Extended European Search Report in European Appln. No. 19746618.8, dated Sep. 14, 2021, 7 pages.
Extended European Search Report in European Appln. No. 21164580.9, dated Oct. 22, 2021, 8 pages.
Iannetta [online], "Nov. 2014 New Products: Wearable coil facilities positioning during prostate MRI," Urology Times, retrieved on Nov. 10, 2014, retrieved from<URL: http://urologytimes.modernmedicine.com/urology-times/news/november-2014-new-products-wearable-coil-facilitates-positioning-during-prostate-mri?page=full>, 7 pages.
IL Office Action in Israeli Appln. No. 256280.0, dated Sep. 16, 2020, 9 pages (with English Translation).
International Preliminary Report on Patentability in International Appln. No. PCT/US2019/016395, dated Aug. 4, 2020, 7 pages.
International Preliminary Report on Patentability in International Appln. No. PCT/US2020/013155, dated Jul. 22, 2021, 8 pages.
International Search Report and Written Opinion in International Appln. No. PCT/US2019/16395, dated Apr. 30, 2019, 13 pages.
O'Driscoll et al., "A mm-Sized implantable power receiver with adaptive link compensation," Poster, Presented at IEEE International Solid-State Circuits Conference, Session 17, 2009, 3 pages.
PCT International Preliminary Report on Patentability and Written Opinion in International Appln. No. PCT/US2012/023029, issued Jan. 28, 2014, 9 pages.
PCT International Preliminary Report on Patentability and Written Opinion in International Appln. No. PCT/US2012/032200 issued Oct. 8, 2013, 11 pages.
PCT International Preliminary Report on Patentability and Written Opinion in International Appln. No. PCT/US2012/048903, issued Mar. 25, 2014, 8 pages.

(56) References Cited

OTHER PUBLICATIONS

PCT International Preliminary Report on Patentability in International Appln. No. PCT/US2013/077846, issued Jun. 30, 2015, 6 pages.
PCT International Preliminary Report on Patentability issued in International Appl. No. PCT/US2012/055746, issued Jan. 2, 2013, 10 pages.
PCT International Preliminary Report on Patentability issued in International Appln. No. PCT/US2012/050633, issued Feb. 18, 2014, 7 pages.
PCT International Search Report and PCT Written Opinion of the International Searching Authority in International Appln. No. PCT/US2012/055746, dated Jan. 3, 2013, 11 pages.
PCT International Search Report and the Written Opinion in Appln. No. PCT/US2012/048903 dated Oct. 10, 2012, 9 pages.
PCT International Search Report and Written Opinion in International Appln. No. PCT/US2012/023029, dated May 16, 2012, 10 pages.
PCT International Search Report and Written Opinion in International Appln. No. PCT/US2012/032200, dated Jul. 27, 2012, 12 pages.
PCT International Search Report and Written Opinion in International Appln. No. PCT/US2012/050633 dated Oct. 23, 2012, 7 pages.
PCT International Search Report and Written Opinion in International Appln. No. PCT/US2013/077846 dated Apr. 21, 2014, 10 pages.
PCT International Search Report and Written Opinion in International Appln. No. PCT/US2020/013155, dated Apr. 1, 2020, 8 pages.
pharad.com [online], "Assembly, Wearable Antenna, 350-450 MHz," retrieved on Oct. 14, 2010, retrieved from URL< http://www.pharad.com/pdf/UHF-Wearable-Antenna-2D.pdf>, 1 page.
Poon et al., "Optimal frequency for wireless power transmission into dispersive tissue," IEEE Transactions on Antennas and Propagation, May 2010, 58(5):1739-1750.
Stensaas et al., "Histopathological evaluation of materials implanted in the cerebral cortex," Acta Neuropathologica, Jan. 1978, 41(2):145-155.
Turner et al., "Cerebral astrocyte response to micromachined silicon implants," Experimental Neurology, Mar. 1999, 156(1):33-49.
Weiland et al., "Chronic neural stimulation with thin-film, iridium oxide electrode," IEEE Transactions on Biomedic Engineering, Jul. 2000, 47(7):911-918.
Williams et al., "Complex impedance spectroscopy for monitoring tissue responses to inserted neural implants," Journal of Neural Engineering, Nov. 2007, 4(4):410-423.
wirelessdesignmag.com [online], "Pharad at Forefront of LTE Antenna Innovation with Development of LTE Wearable Antenna," retrieved on Aug. 12, 2012, retrieved from<URL:http://www.wirelessdesignmag.com/product-release/2013/08/pharad-forefront-lte-antenna-innovation-development-lte-wearable-antenna>, 3 pages.
Extended European Search Report in European Appln No. 20738285.4, dated Aug. 17, 2022, 5 pages.

\* cited by examiner

Transmit a first set of radio-frequency (RF) pulses to an implantable wireless stimulator device such that electric currents are created from the first set of RF pulses and flown through a calibrated internal load on the implantable wireless stimulator device 502

In response to the electric currents flown through the calibrated internal load, record a first set of RF reflection measurements 504

Transmit a second set of radio-frequency (RF) pulses to the implantable wireless stimulator device such that stimulation currents are created from the second set of RF pulses and flown through an electrode of the implantable wireless stimulator device to tissue surrounding the electrode 506

In response to the stimulation currents flown through the electrode to the surrounding tissue, record a second set of RF reflection measurements 508

Characterize an electrode-tissue impedance by comparing the second set of RF reflection measurements with the first set of RF reflections measurements 510

FIG. 5

SYSTEMS AND METHODS TO SENSE STIMULATION ELECTRODE TISSUE IMPEDANCE

RELATED APPLICATIONS

This application is a continuation of U.S. application Ser. No. 16/265,669, filed Feb. 1, 2019, which claims the benefit of U.S. Provisional Application Ser. No. 62/624,982, filed Feb. 1, 2018. Both of these prior applications are incorporated by reference in their entirety.

TECHNICAL FIELD

This application relates generally to systems and methods to operation of an implantable stimulator device that has been implanted inside a subject.

BACKGROUND

Modulation of excitable tissue in the body by electrical stimulation has become an important type of therapy for patients with chronic disabling conditions, including pain, movement initiation and control, involuntary movements, vascular insufficiency, heart arrhythmias and various other modalities. A variety of therapeutic intra-body electrical stimulation techniques can be utilized to provide therapeutic relief for these conditions. For instance, devices may be used to deliver stimulatory signals to excitable tissue, record vital signs, perform pacing or defibrillation operations, record action potential activity from targeted tissue, control drug release from time-release capsules or drug pump units, or interface with the auditory system to assist with hearing.

SUMMARY

In one aspect, some implementations provide a method to adjust stimulation by an implantable wireless stimulator device to surrounding tissue, the method including: transmitting, from an external pulse generator and via electric radiative coupling, a first set of radio-frequency (RF) pulses to the implantable wireless stimulator device such that electric currents are created from the first set of RF pulses and flown through a calibrated internal load on the implantable wireless stimulator device; in response to the electric currents flown through the calibrated internal load, recording, on the external pulse generator, a first set of RF reflection measurements; transmitting, from the external pulse generator and via electric radiative coupling, a second set of radio-frequency (RF) pulses to the implantable wireless stimulator device such that stimulation currents are created from the second set of RF pulses and flown through an electrode of the implantable wireless stimulator device to tissue surrounding the electrode; in response to the stimulation currents flown through the electrode to the surrounding tissue, recording, on the external pulse generator, a second set of RF reflection measurements; and characterizing an electrode-tissue impedance by comparing the second set of RF reflection measurements with the first set of RF reflections measurements.

Implementations may include one or more of the following features. In response to characterizing the electrode-tissue impedance as resistive, the method may include adjusting one or more input pulses to be transmitted by the external pulse generator to the implantable wireless stimulator device such that stimulus currents created from the input pulses on the implantable wireless stimulator device are adjusted to compensate for a resistive electrode-tissue impedance. Adjusting input pulses may include: maintaining a steady-state delivery of electrical power to the implantable wireless stimulator device such that electrical energy is extracted from the input pulses as fast as electrical energy is consumed by the implantable wireless stimulator device to (i) generate the stimulus currents with one or more pulse parameters that have been varied to accommodate the resistive electrode-tissue impedance, and (ii) deliver the stimulus currents from the electrode on the implantable wireless stimulator device to the surrounding tissue. The pulse parameters may include: a pulse width, a pulse amplitude, and a pulse frequency.

The method may include: in response to characterizing the electrode-tissue impedance as capacitive, adjusting one or more input pulses to be transmitted by the external pulse generator to the implantable wireless stimulator device such that stimulus currents created from the input pulses and delivered by the electrode on the implantable wireless stimulator device to the surrounding tissue are adjusted to compensate for a capacitive electrode-tissue impedance. Adjusting input pulses may include: maintaining a steady-state delivery of electrical power to the implantable wireless stimulator device such that electrical energy is extracted from the input pulses as fast as electrical energy is consumed by the implantable wireless stimulator device to (i) generate the stimulus currents with one or more pulse parameters that have been varied to accommodate the capacitive electrode-tissue impedance, and (ii) deliver the stimulus currents from the electrode on the implantable wireless stimulator device to the surrounding tissue. The pulse parameters may include: a pulse width, a pulse amplitude, and a pulse frequency.

The method may further include: based on results of characterizing the electrode-tissue impedance, automatically choosing a stimulation session by determining input pulses to be transmitted by the external pulse generator to the implantable wireless stimulator device such that stimulus currents are created on the implantable wireless stimulator device and delivered by the electrode on the implantable wireless stimulator device to the surrounding tissue. Determining input pulses may include: updating the second set of radio-frequency (RF) pulses to obtain updated second set of RF reflection measurements; and comparing the updated second set of RF reflection measurements with the first set of RF reflection measurements. Updating and comparing may be performed iteratively until desired RF reflection measurements are obtained.

The method may further include: automatically performing fault checking according to results of characterizing the electrode-tissue impedance. Automatically performing fault checking may include: detecting a damaged wire in a circuit leading to the electrode on the implantable wireless stimulator device.

In another aspect, some implementations provide a system that includes: an implantable wireless stimulator device including: a first non-inductive antenna; one or more electrodes; and a circuit between the first non-inductive antenna and the one or more electrodes, the circuit comprising: a calibrated internal load that represents a pre-determined load condition on the one or more electrodes; an external pulse generator including: a second non-inductive antenna configured to: transmit, via electric radiative coupling, a first set of radio-frequency (RF) pulses to the first non-inductive antenna on the implantable wireless stimulator device such that electric currents are created from the first set of RF pulses and flown through the calibrated internal load on the implantable wireless stimulator device; and transmit, via electric radiative coupling, a second set of radio-frequency (RF) pulses to the first non-inductive antenna on the implantable wireless stimulator device such that stimulation currents are created from the second set of RF pulses and flown through an electrode of the implantable wireless stimulator device to tissue surrounding the electrode; and a reflection sensor subs-system coupled to the second non-inductive antenna and configured to: in response to the electric currents flown through the calibrated internal load, obtain a first set of RF reflection measurements; and in response to the stimulation currents flown through the electrode to the surrounding tissue, obtain a second set of RF reflection measurements; and a signal processor in communication with the reflection sensor subs-system and configured to: characterize an electrode-tissue impedance by comparing the second set of RF reflection measurements with the first set of RF reflections measurements.

Implementations may include one or more of the following features. The reflection sensor subs-system includes: a directional coupler coupled to the second non-inductive antenna and configured to detect a radio frequency (RF) signal reflected from the first non-inductive antenna; and a radio frequency (RF) phase detector coupled to the directional coupler and configured to detect phase differences between the RF signal reflected from the first non-inductive antenna and an RF signal transmitted from the second non-inductive antenna to the first non-inductive antenna. The reflection sensor subs-system may further include: an analog-to-digital converter (ADC) coupled to the directional coupler and configured to convert the RF signal reflected from the first non-inductive antenna into digital recordings.

The signal processor may be a digital signal processor. The signal processor may be further configured to: in response to characterizing the electrode-tissue impedance as resistive, adjust one or more input pulses to be transmitted by the external pulse generator to the implantable wireless stimulator device such that one or more stimulus pulses created from the input pulses and delivered by the electrode on the implantable wireless stimulator device to the surrounding tissue are adjusted to compensate for a resistive electrode-tissue impedance. The signal processor may be further configured to: in response to characterizing the electrode-tissue impedance as capacitive, adjust one or more input pulses to be transmitted by the external pulse generator to the implantable wireless stimulator device such that stimulus currents created from the input pulses and delivered by the electrode on the implantable wireless stimulator device to the surrounding tissue are adjusted to compensate for a capacitive electrode-tissue impedance. The signal processor may be further configured to: based on results of characterizing the electrode-tissue impedance, automatically choose a stimulation session by determining input pulses to be transmitted by the external pulse generator to the implantable wireless stimulator device such that stimulus currents are created on the implantable wireless stimulator device and delivered by the electrode on the implantable wireless stimulator device to the surrounding tissue. The signal processor may be further configured to: automatically perform fault checking according to results of characterizing the electrode-tissue impedance.

BRIEF DESCRIPTION OF THE DRAWINGS

FIG. 5 illustrates an example of a flow chart.

Like reference symbols in the various drawings indicate like elements.

DETAILED DESCRIPTION

Figure 1:
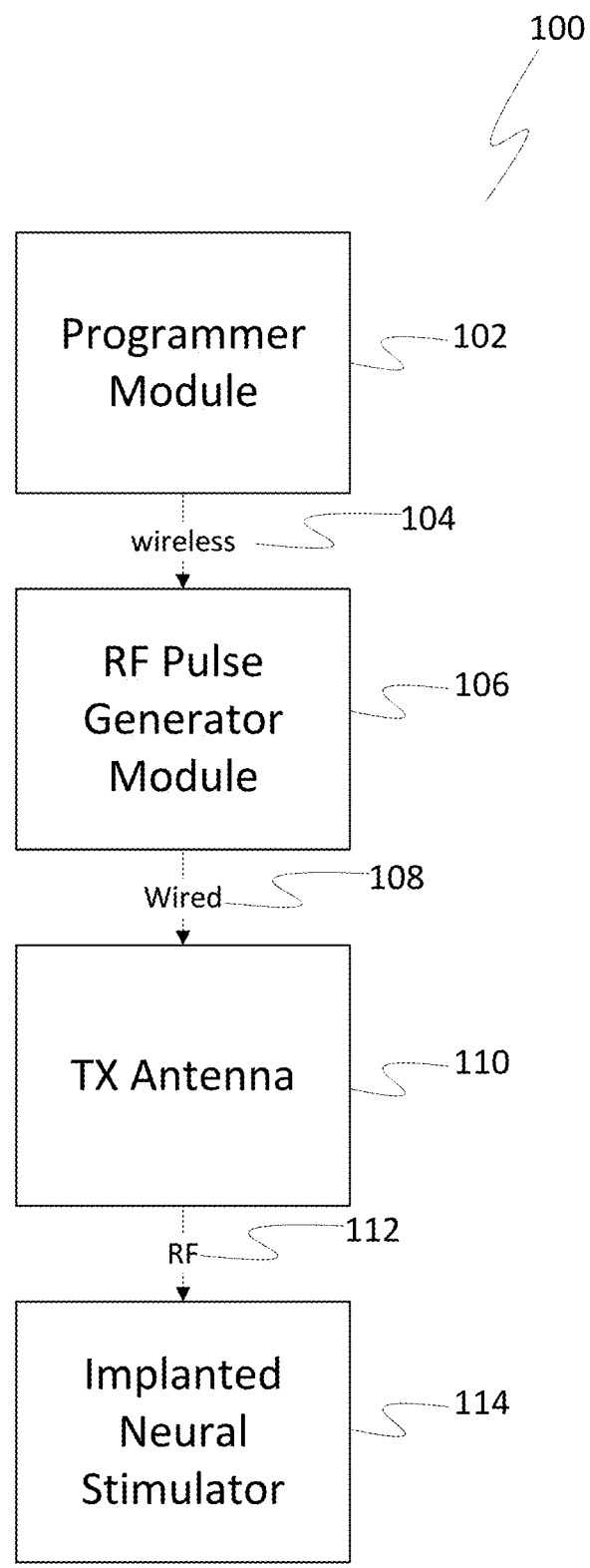
FIG. 1 depicts a high-level diagram of an example of a wireless stimulation system.

In various implementations, systems and methods are disclosed for applying one or more electrical impulses to targeted excitable tissue, such as nerves, for treating chronic pain, inflammation, arthritis, sleep apnea, seizures, incontinence, pain associated with cancer, incontinence, problems of movement initiation and control, involuntary movements, vascular insufficiency, heart arrhythmias, obesity, diabetes, craniofacial pain, such as migraines or cluster headaches, and other disorders. In certain embodiments, a device may be used to send electrical energy to targeted nerve tissue by using remote radio frequency (RF) energy without cables or inductive coupling to power an implanted wireless stimulator device. The targeted nerves can include, but are not limited to, the spinal cord and surrounding areas, including the dorsal horn, dorsal root ganglion, the exiting nerve roots, nerve ganglions, the dorsal column fibers and the peripheral nerve bundles leaving the dorsal column and brain, such as the vagus, occipital, trigeminal, hypoglossal, sacral, coccygeal nerves and the like.

A wireless stimulation system can include an implantable stimulator device with one or more electrodes and one or more conductive antennas (for example, dipole or patch antennas), and internal circuitry for detecting pulse instructions, and rectification of RF electrical energy. The system may further comprise an external controller and antenna for transmitting radio frequency or microwave energy from an external source to the implantable stimulator device with neither cables nor inductive coupling to provide power.

In various implementations, the wireless implantable stimulator device is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling, and the received RF power is used to power the implantable stimulator device. This allows such devices to produce electrical currents capable of stimulating nerve bundles without a physical connection to an implantable pulse generator (IPG) or use of an inductive coil.

In some implementations, a passive relay module may be configured as an implantable device to couple electromagnetic energy radiated from an external transmitting antenna to a wireless implantable stimulator device. In one example, the implantable device includes two monopole coupler arms connected to each other by a cable. One monopole coupler arm may be implanted in a parallel configuration with the external transmitting antenna such that linearly polarized electromagnetic waves radiated from the external transmitting antenna are received by this monopole coupler arm. Through the cable, the received electromagnetic waves may propagate to the other monopole coupler arm. In a reciprocal manner, this monopole coupler arm may radiate the received electromagnetic energy to the receiving antenna of the stimulator device. To effectively radiate the received electromagnetic energy to the receiving antenna of the stimulator device, parallel alignment of this other monopole coupler arm and the receiving antenna again may be used. In some cases, lengths of the monopole arms and length of the cable can be tailored to improve transmission efficiency, for example, at a particular operating frequency.

Some implementations utilize non-battery wireless power transfer implants, a new class of devices that can be constructed in very small form factors, enabling a minimal surgical incision and potentially unlimited product life, free of limitations and complications associated with battery powered devices. However, wireless power transfer faces various challenges. An implanted antenna is ideally very small in size to pass through a needle or cannula in order to enable a minimally invasive surgery. Generally a small antenna receives less RF power than a larger antenna, meaning the efficiency of power transfer to a very small antenna can be poor. Compounding the problem is the limited RF power that can be delivered by the external transmitting source because the Specific Absorption Rate (SAR) of RF inside the human body must be kept within safety limits. As such, optimum power transfer efficiency (or minimum path loss) must be maintained during wireless power transfer for implantable medical devices. To affect optimum power transfer, the external transmitting antenna must be aligned on the body in a favorable position relative to the implant. Estimating the location of the implant was historically only feasible using a medical imaging system, such as x-ray or ultrasound. Some implementations disclosed herein enable locating the in-situ receiver antenna, without the use of complex and expensive medical imaging techniques.

Further descriptions of exemplary wireless systems for providing neural stimulation to a patient can be found in commonly-assigned, published PCT applications PCT/US2012/23029 filed Jan. 28, 2011 and published Aug. 2, 2012, PCT/US2012/32200 filed Apr. 11, 2011 and published Oct. 11, 2012, PCT/US2012/48903, filed Jan. 28, 2011 and published Feb. 7, 2013, PCT/US2012/50633, filed Aug. 12, 2011 and published Feb. 21, 2013 and PCT/US2012/55746, filed Sep. 15, 2011 and published Mar. 21, 2013, the complete disclosures of which are incorporated by reference.

FIG. 1 depicts a high-level diagram of an example of a wireless stimulation system. The wireless stimulation system may include four major components, namely, a programmer module 102, a RF pulse generator module 106, a transmitting (TX) antenna 110 (for example, a patch antenna, slot antenna, or a dipole antenna), and an implanted wireless stimulator device 114. The programmer module 102 may be a computer device, such as a smart phone, running a software application that supports a wireless connection 104, such as Bluetooth®. The application can enable the user to view the system status and diagnostics, change various parameters, increase/decrease the desired stimulus amplitude of the electrical pulses, and adjust feedback sensitivity of the RF pulse generator module 106, among other functions.

The RF pulse generator module 106 may include communication electronics that support the wireless connection 104 and the battery to power the generator electronics. In some implementations, the RF pulse generator module 106 includes the TX antenna embedded into its packaging form factor, while in other implementations, the TX antenna is connected to the RF pulse generator module 106 through a wired connection 108 or a wireless connection (not shown). The TX antenna 110 may be coupled directly to tissue to create an electric field that powers the implanted wireless stimulator device 114. The TX antenna 110 communicates with the implanted wireless stimulator device 114 through an RF interface. For instance, the TX antenna 110 radiates an RF transmission signal that is modulated and encoded by the RF pulse generator module 110. The implanted wireless stimulator device of module 114 contains one or more antennas, such as dipole antenna(s), to receive and transmit through RF interface 112. In particular, the coupling mechanism between antenna 110 and the one or more antennas on the implanted wireless stimulation device of module 114 utilizes electrical radiative coupling and not inductive coupling. In other words, the coupling is through an electric field rather than a magnetic field.

Through this electrical radiative coupling, the TX antenna 110 can provide an input signal to the implanted wireless stimulator device 114. This input signal contains energy and may contain information encoding stimulus waveforms to be applied at the electrodes of the implanted wireless stimulator device 114. In some implementations, the power level of this input signal directly determines an applied amplitude (for example, power, current, or voltage) of the one or more electrical pulses created using the electrical energy contained in the input signal. Within the implanted wireless stimulator device 114 are components for demodulating the RF transmission signal, and electrodes to deliver the stimulation to surrounding neural tissue.

The RF pulse generator module 106 can be implanted subcutaneously, or it can be worn external to the body. When external to the body, the RF generator module 106 can be incorporated into a belt or harness design to allow for electric radiative coupling through the skin and underlying tissue to transfer power and/or control parameters to the implanted wireless stimulator device 114. In either event, receiver circuit(s) internal to the wireless stimulator device 114 can capture the energy radiated by the TX antenna 110 and convert this energy to an electrical waveform. The receiver circuit(s) may further modify the waveform to create an electrical pulse suitable for the stimulation of neural tissue.

In some implementations, the RF pulse generator module 106 can remotely control the stimulus parameters (that is, the parameters of the electrical pulses applied to the neural tissue) and monitor feedback from the wireless stimulator device 114 based on RF signals received from the implanted wireless stimulator device 114. A feedback detection algorithm implemented by the RF pulse generator module 106 can monitor data sent wirelessly from the implanted wireless stimulator device 114, including information about the energy that the implanted wireless stimulator device 114 is receiving from the RF pulse generator and information about the stimulus waveform being delivered to the electrodes. In order to provide an effective therapy for a given medical condition, the system can be tuned to provide the optimal amount of excitation or inhibition to the nerve fibers by electrical stimulation. A closed loop feedback control method can be used in which the output signals from the implanted wireless stimulator device 114 are monitored and used to determine the appropriate level of neural stimulation for maintaining effective therapy, or, in some cases, open loop control can be used.

Figure 2:
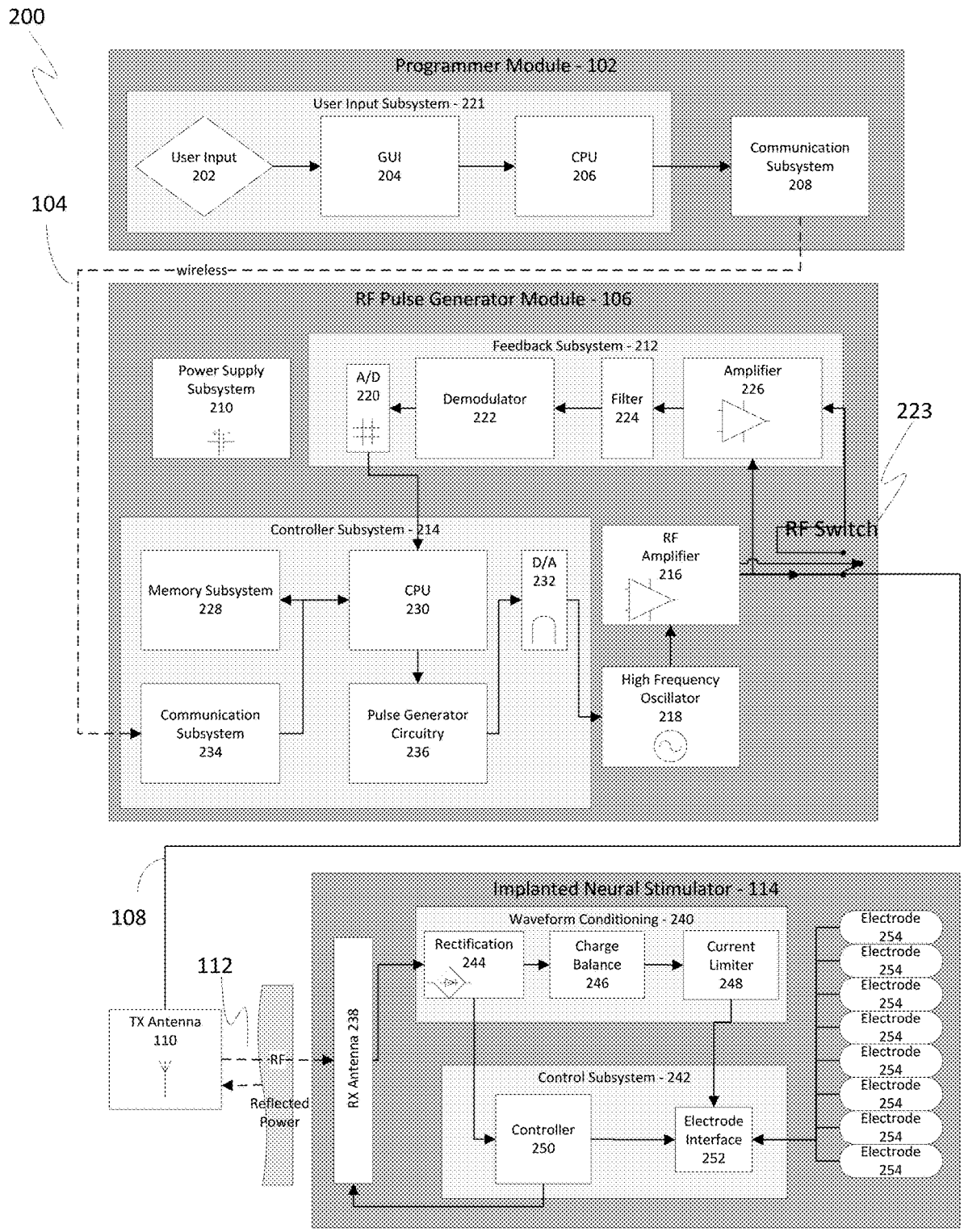
FIG. 2 depicts a more detailed diagram of an example of the wireless stimulation system.

FIG. 2 depicts a detailed diagram of an example of the wireless stimulation system. As depicted, the programming module 102 may comprise user input system 202 and communication subsystem 208. The user input system 221 may allow various parameter settings to be adjusted (in some cases, in an open loop fashion) by the user in the form of instruction sets. The communication subsystem 208 may transmit these instruction sets (and other information) via the wireless connection 104, such as Bluetooth or Wi-Fi, to the RF pulse generator module 106, as well as receive data from module 106.

For instance, the programmer module 102, which can be utilized for multiple users, such as a patient's control unit or clinician's programmer unit, can be used to send stimulation parameters to the RF pulse generator module 106. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

TABLE 1

Stimulation Parameter

| | |
|---|---|
| Pulse Amplitude: | 0 to 25 mA |
| Pulse Frequency: | 0 to 20000 Hz |
| Pulse Width: | 0 to 2 ms |

The RF pulse generator module 106 may be initially programmed to meet the specific parameter settings for each individual patient during the initial implantation procedure. Because medical conditions or the tissue properties can change over time, the ability to re-adjust the parameter settings may be beneficial to ensure ongoing efficacy of the neural modulation therapy.

The programmer module 102 may be functionally a smart device and associated application. The smart device hardware may include a CPU 206 and be used as a vehicle to handle touchscreen input on a graphical user interface (GUI) 204, for processing and storing data.

The RF pulse generator module 106 may be connected via wired connection 108 to an external TX antenna 110. Alternatively, both the antenna and the RF pulse generator are located subcutaneously (not shown).

The signals sent by RF pulse generator module 106 to the implanted wireless stimulator device 114 may include both power and parameter-setting attributes in regards to stimulus waveform, amplitude, pulse width, and frequency. The RF pulse generator module 106 can also function as a wireless receiving unit that receives feedback signals from the implanted wireless stimulator device 114. To that end, the RF pulse generator module 106 may contain microelectronics or other circuitry to handle the generation of the signals transmitted to the device 114 as well as handle feedback signals, such as those from the stimulator device 114. For example, the RF pulse generator module 106 may comprise controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, communication subsystem 234 to communicate with programmer module 102 (including receiving stimulation parameters from programmer module), pulse generator circuitry 236, and digital/analog (D/A) converters 232.

The controller subsystem 214 may be used by the patient and/or the clinician to control the stimulation parameter settings (for example, by controlling the parameters of the signal sent from RF pulse generator module 106 to the stimulator device 114). These parameter settings can affect, for example, the power, current level, or shape of the one or more electrical pulses. The programming of the stimulation parameters can be performed using the programming module 102, as described above, to set the repetition rate, pulse width, amplitude, and waveform that will be transmitted by RF energy to the receiving (RX) antenna 238, typically a dipole antenna (although other types may be used), in the implanted wireless stimulation device 214. The clinician may have the option of locking and/or hiding certain settings within the programmer interface, thus limiting the patient's ability to view or adjust certain parameters because adjustment of certain parameters may require detailed medical knowledge of neurophysiology, neuro-anatomy, protocols for neural modulation, and safety limits of electrical stimulation.

The controller subsystem 214 may store received parameters in the local memory subsystem 228, until the parameters are modified by new data received from the programming module 102. The CPU 206 may use the parameters stored in the local memory to control the RF pulse generator circuitry 236 to generate a pulse timing waveform that is modulated by a high frequency oscillator 218 in the range from 300 MHz to 8 GHz (preferably between about 700 MHz and 5.8 GHz and more preferably between about 800 MHz and 1.3 GHz). The resulting RF signal may then be amplified by RF amplifier 226 and then sent through an RF switch 223 to the TX antenna 110 to reach through depths of tissue to the RX antenna 238.

In some implementations, the RF signal sent by TX antenna 110 may simply be a power transmission signal used by the wireless stimulation device module 114 to generate electric pulses. In other implementations, a digital signal may also be transmitted to the wireless stimulator device 114 to send instructions about the configuration of the wireless stimulator device 114. The digital signal is used to modulate the carrier signal that is coupled onto the implanted antenna(s) 238 and does not interfere with the input received on the same stimulator device to power the device. In one embodiment the digital signal and powering signal are combined into one signal, where the digital signal is used to modulate the RF powering signal, and thus the wireless stimulation device is powered directly by the received digital signal; separate subsystems in the wireless stimulation device harness the power contained in the signal and interpret the data content of the signal.

The RF switch 223 may be a multipurpose device such as a dual directional coupler, which passes the RF pulses to the TX antenna 110 with minimal insertion loss while simultaneously providing two low-level outputs to the feedback subsystem 212; one output delivers a forward power signal to the feedback subsystem 212, where the forward power signal is an attenuated version of the RF pulse sent to the TX antenna 110, and the other output delivers a reverse power signal to a different port of the feedback subsystem 212, where reverse power is an attenuated version of the reflected RF energy from the TX Antenna 110. The reflected RF energy and/or RF signals from the wireless stimulator device 114 are processed in the feedback subsystem 212.

The feedback subsystem 212 of the RF pulse generator module 106 may include reception circuitry to receive and extract telemetry or other feedback signals from the wireless stimulator device 114 and/or reflected RF energy from the signal sent by TX antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the RF pulse generator 106. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can for example be used to detect fault conditions in the RF-power delivery system. In an ideal condition, when the TX antenna 110 has perfectly matched impedance to the tissue that it contacts, the electromagnetic waves generated from the RF pulse generator 106 pass unimpeded from the TX antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the TX antenna 110 with the body surface. When such a mismatch occurs, the electromagnetic waves sent from the RF pulse generator 106 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the RF pulse generator 106. For example, for a moderate degree of reflected power the course of action can be for the controller subsystem 214 to increase the amplitude of RF power sent to the TX antenna 110, as would be needed to compensate for slightly non-optimum but acceptable TX antenna coupling to the body. For higher ratios of reflected power, the course of action can be to prevent operation of the RF pulse generator 106 and set a fault code to indicate that the TX antenna 110 has little or no coupling with the body. This type of reflected-power fault condition can also be generated by a poor or broken connection to the TX antenna. In either case, it may be desirable to stop RF transmission when the reflected-power ratio is above a defined threshold, because internally reflected power can result in unwanted heating of internal components, and this fault condition means the system cannot deliver sufficient power to the implanted wireless stimulation device and thus cannot deliver therapy to the user.

The controller 242 of the wireless stimulator device 114 may transmit informational signals, such as a telemetry signal, through the antenna 238 to communicate with the RF pulse generator module 106. For example, the telemetry signal from the wireless stimulator device 114 may be coupled to its dipole antenna(s) 238. The antenna(s) 238 may be connected to electrodes 254 in contact with tissue to provide a return path for the transmitted signal. An A/D (not shown) converter can be used to transfer stored data to a serialized pattern that can be transmitted on the pulse-modulated signal from the internal antenna(s) 238 of the wireless stimulator device 114.

A telemetry signal from the implanted wireless stimulator device 114 may include stimulus parameters such as the power or the amplitude of the current that is delivered to the tissue from the electrodes. The feedback signal can be transmitted to the RF pulse generator module 116 to indicate the strength of the stimulus at the nerve bundle by means of coupling the signal to the implanted RX antenna 238, which radiates the telemetry signal to the external (or remotely implanted) RF pulse generator module 106. The feedback signal can include either or both an analog and digital telemetry pulse modulated carrier signal. Data such as stimulation pulse parameters and measured characteristics of stimulator performance can be stored in an internal memory device within the implanted stimulator device 114, and can be sent via the telemetry signal. The frequency of the carrier signal may be in the range of at 300 MHz to 8 GHz (preferably between about 700 MHz and 5.8 GHz and more preferably between about 800 MHz and 1.3 GHz).

In the feedback subsystem 212, the telemetry signal can be down-modulated using demodulator 222 and digitized through an analog to digital (A/D) converter 220. The digital telemetry signal may then be routed to a CPU 230 for interpretation. The CPU 230 of the controller subsystem 214 can compare the reported stimulus parameters to those held in local memory 228 to verify the wireless stimulator device 114 delivered the specified stimuli to tissue. For example, if the wireless stimulation device reports a lower current than was specified, the power level from the RF pulse generator module 106 can be increased so that the implanted wireless stimulator device 114 will have more available power for stimulation. The implanted wireless stimulator device 114 could alternatively generate telemetry data in real time, for example, at a rate of 8 Kbits per second. All feedback data received from the implanted stimulator device 114 can be logged against time and sampled to be stored for retrieval to a remote monitoring system accessible by the health care professional.

The RF signals received by the internal antenna(s) 238 may be conditioned into waveforms that are controlled within the implantable wireless stimulator device 114 by the control subsystem 242 and routed to the appropriate electrodes 254 that are placed in proximity to the tissue to be stimulated. For instance, the RF signal transmitted from the RF pulse generator module 106 may be received by RX antenna 238 and processed by circuitry, such as waveform conditioning circuitry 240, within the implanted wireless stimulator device 114 to be converted into electrical pulses applied to the electrodes 254 through electrode interface 252. In some implementations, the implanted wireless stimulator device 114 contains between two to sixteen electrodes 254.

The waveform conditioning circuitry 240 may include a rectifier 244. The rectified signal may be fed to the controller 242 for receiving encoded instructions from the RF pulse generator module 106. The rectified signal may also be fed to a charge balance component 246 that is configured to create one or more electrical pulses such that the one or more electrical pulses result in a charge balanced electrical stimulation waveform at the one or more electrodes. The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations. Generally, for a given electrode having several square millimeters surface area, it is the charge per phase that should be limited for safety (where the charge delivered by a stimulus phase is the integral of the current). But, in some cases, the limit can instead be placed only on the current amplitude. The current limiter 248 can automatically limit or "clip" the stimulus phase to maintain the phase within the safety limit.

The controller 250 of the stimulator 205 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 106 has multiple electrodes 254 in contact with tissue, and for a given stimulus the RF pulse generator module 106 can assign one or more electrodes to 1) act as a stimulating electrode, 2) act as a return electrode, or 3) be inactive. The assignment can be effectuated by virtue of RF pulse generator module 106 sending instructions to the implantable stimulator 205.

Also, in some implementations, for a given stimulus pulse, the controller 250 may control the electrode interface 252 to divide the current among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be manipulated. A given stimulus waveform may be initiated and terminated at selected times, and this time course may be synchronized across all stimulating and return electrodes; further, the frequency of repetition of this stimulus cycle may be synchronous for all the electrodes. However, controller 250, on its own or in response to instructions from pulse generator 106, can control electrode interface 252 to designate one or more subsets of electrodes to deliver stimulus waveforms with non-synchronous start and stop times, and the frequency of repetition of each stimulus cycle can be arbitrarily and independently specified.

In some implementations, the controller 250 can arbitrarily shape the stimulus waveform amplitude, and it may do so in response to instructions from pulse generator 106. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, the wireless stimulator device 114 may include a charge-balancing component 246. Biphasic stimulating current pulses ensure that no net charge appears at the electrode after each stimulation cycle and the electrochemical processes are balanced to prevent net DC currents. The wireless stimulator device 114 may be configured to ensure that the resulting stimulus waveform has a net zero charge. Charge balanced stimuli are thought to have minimal damaging effects on tissue by reducing or eliminating electrochemical reaction products created at the electrode-tissue interface.

In some implementations, the charge balance component 246 uses a DC-blocking capacitor(s) placed electrically in series with the stimulating electrodes and body tissue, between the point of stimulus generation within the stimulator circuitry and the point of stimulus delivery to tissue. In a multi-electrode stimulator, one charge-balance capacitor(s) may be used for each electrode or a centralized capacitor(s) may be used within the stimulator circuitry prior to the point of electrode selection. The stimulus waveform created prior to the charge-balance capacitor, called the drive waveform, may be controlled such that its amplitude is varied during the duration of the drive pulse. The shape of the stimulus waveform may be modified in this fashion to create a physiologically advantageous stimulus.

In some implementations, the wireless stimulator device 114 may create a drive-waveform envelope that follows the envelope of the RF pulse received by the receiving dipole antenna(s) 238. In this case, the RF pulse generator module 106 can directly control the envelope of the drive waveform within the wireless stimulator device 114, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted wireless stimulator device 114 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect.

In some implementations, the amplitude and timing of stimulus and charge-balancing phases is controlled by the amplitude and timing of RF pulses from the RF pulse generator module 106, and in others this control may be administered internally by circuitry onboard the wireless stimulator device 114, such as controller 250. In the case of onboard control, the amplitude and timing may be specified or modified by data commands delivered from the pulse generator module 106.

Figure 3A:
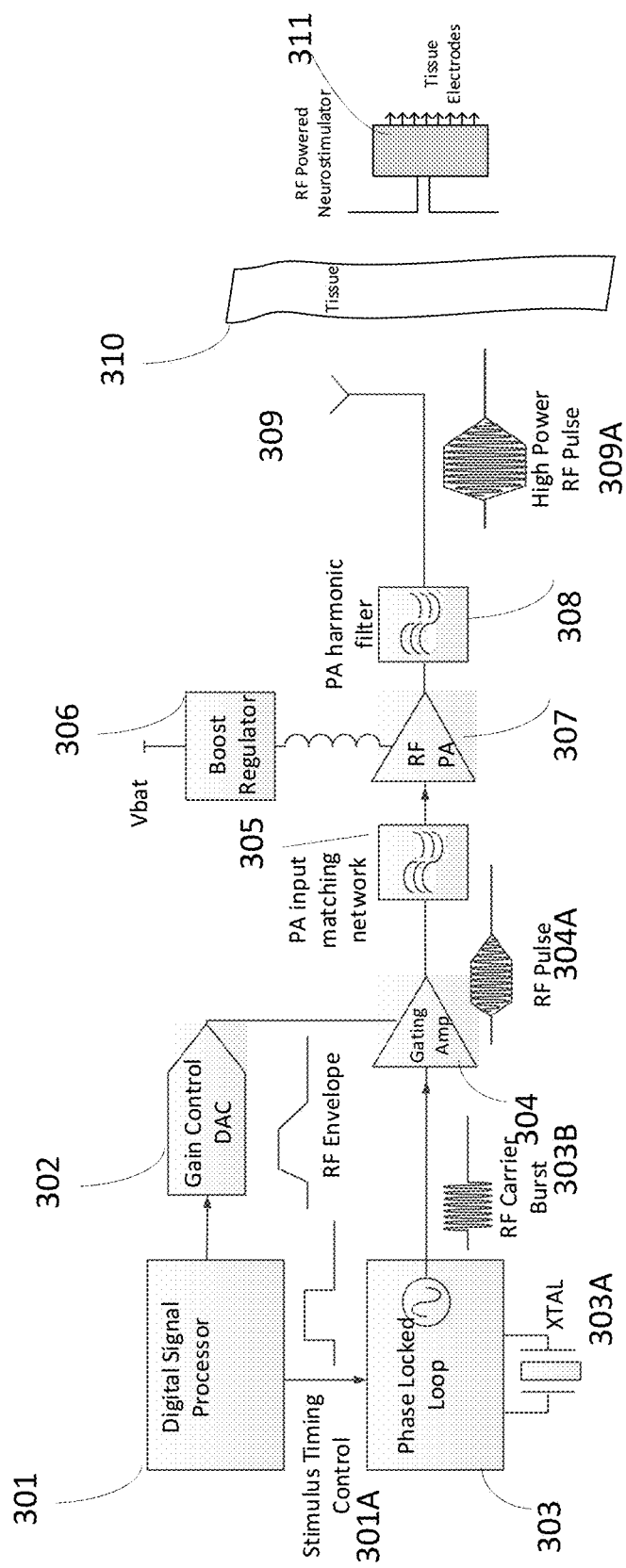
FIG. 3A is an illustration of an example of an implementation of the microwave field stimulator (MFS) transmitter for wireless power transfer to an implanted dipole antenna.
Figure 3B:
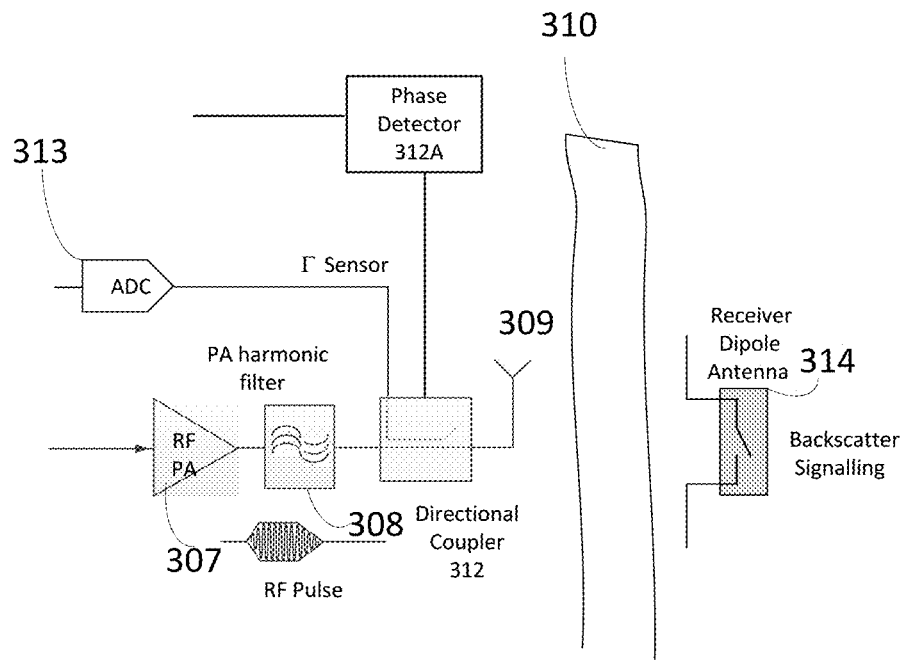
FIG. 3B is another illustration of another example of the implementation with a directional coupler and power detector.

Referring to FIGS. 3A to 3B, some implementation use the microwave field stimulator (MFS) transmitter for wireless power transfer, as illustrated in system level diagram 300. The MFS may include a digital signal processor 301, gain control 302, phase-locked loop 303, gating amplifier 304, pulse-amplitude input matching network 305, boost regulator 306, radio-frequency (RF) amplifier 307, pulse-amplitude harmonic filter 308, antenna 309, tissue boundary 310, passive neural stimulator 311, directional coupler 312, analog-digital converter (ADC) 313, and receiving dipole antenna 314. As illustrated, implanted electrodes may be used to pass pulsatile electrical currents of controllable frequency, pulse width and amplitudes. A variety of therapeutic intra-body electrical stimulation techniques may be utilized to treat conditions that are known to respond to neural modulation.

Digital signal processor 301 may generate pulse parameters such as pulse width, amplitude, and repetition rate. Digital signal processor 301 may feed pulse parameters to gain control 302, which can include a digital to analog converter (DAC). Gain control 302 may generate RF envelope 302A to gating amplifier 304. Digital signal processor 301 may feed phase-locked loop 303 with stimulus timing control 301A, which is a voltage signal that drives crystal XTAL 303A to generate RF carrier burst 303B. RF carrier burst 303B arrives at gating amplifier to modulate RF envelope 302A such that RF pulse 304A is generated to feed pulse-amplitude input matching network 305.

Output from pulse-amplitude input matching network 305 is provided to RF amplifier 307 under a bias voltage from boost regulator 306. Subsequently, a harmonic filter 308 mitigates harmonic distortions and feeds the filtered output as a high power RF pulse to antenna 309. The high power RF pulse is transmitted from antenna 309 through skin layer 310 to reach receiver dipole antenna 314 of the implanted neural stimulator device 311 so that therapies are applied at tissue electrodes.

In some implementations, the Rx antenna 238 and Tx antenna 110 may exhibit mutual coupling. In some implementations the mutual coupling of the Rx antenna 238 and Tx antenna 110 may be observed for the purpose of assessing the state of the Implanted Neural Stimulator 114.

In some implementations an estimated geometric factor may be included in the measurement normalization that may account for the change in mutual coupling for various thicknesses of tissue that separates the Rx antenna 238 from the Tx antenna 110.

Some implementations incorporate RF complex impedance measurement via Γ Sensor subsystem, which may include an RF phase detector 312A, shown in FIG. 3B. The reflected RF signal is received at antenna 110 and routed via directional coupler 312 to analog-digital converter (ADC) 313, and from this signal the RF impedance, or reflection coefficient, may be calculated.

In some implementations, the wireless stimulation system 100 may utilize the RF reflection measurements to obtain the impedance at the electrode-tissue interface of FIG. 3A. At the implantation site, the extracellular environment around implanted electrodes can change due to insertion-related damage and the presence of the electrodes (foreign material) in the tissue, both of which instigate formation of scar tissue, a compact sheath of cells and extracellular matrix surrounding the implant. Some studies have found that this encapsulating tissue can alter electrical impedance relative to normal (or unscarred) tissue. Since a change of the electrode-tissue impedance may alter the effectiveness of the Implanted Neural Stimulator 114, it would be advantageous for the wireless stimulation system 100 to have the capability of assessing the impedance of the electrode-tissue interface.

In some implementations, based on the deduced impedance of the electrode-tissue interface, the strategy for stimulation can be modified to compensate for the impedance. For example, if the electrode-tissue impedance is found to be highly resistive, the wireless stimulation system 100 may compensate by providing higher voltage to the current driver within the Implantable Neural Stimulator 114.

As discussed in detail through FIGS. 1-2, the RF waveform 112 is received by the stimulator's Rx antenna 238 and subsequently rectified via an RF-to-DC bridge 244 connected to the feed point of the Rx antenna. The received energy is stored in a capacitor in the Implantable Neural Stimulator 114. The energy stored in the capacitor is a function of the charge held by the capacitor and the voltage across the capacitor.

In some implementations, the signal received at the Γ Sensor of FIG. 3B is processed to deduce the state of charge of the capacitor in the Implanted Neural Stimulator 114. In more detail, the time-varying currents and voltages at the rectifier and capacitor act to create a variable RF impedance at the feed point of Rx antenna 238. When the capacitor has low charge, the RF current flows freely across the bridge 244, which is a near RF short circuit at the feed point. When the capacitor approaches full charge, the RF current is impeded, such that there is a near RF open circuit at the feed point. It follows that the complex impedance at the feed point of Rx antenna 238 is an indicator of the state of charge of the capacitor in the Implanted Neural Stimulator 114. Because the dynamic impedance at the Rx antenna is coupled to the Tx antenna 110, the impedance at the Rx antenna can be observed by the Γ Sensor of FIG. 3B, and from this measurement, the RF pulse generator module 106 can deduce the charge of the capacitor in the Implanted Neural Stimulator 114.

In some implementations, the transmitted RF signal 112 can be judiciously selected to maintain the voltage on the capacitor in the Implanted Neural Stimulator 114 at a desired, constant level. For example, the RF pulse rate and width can be strategically selected to maintain a steady-state delivery of power to the stimulator such that energy is delivered at the same rate that it is consumed by the stimulator circuitry.

In some implementations, the state of charge of the capacitor in the Implanted Neural Stimulator 114 is an indicator of the stimulator's present operational state and environment. The voltage at the capacitor will decay proportionally to the rate at which energy is depleted by the load connected to the capacitor. The load may encompass the load at the stimulator's electrodes (the tissue) and the load of the circuitry associated with transferring charge from the capacitor to the electrodes.

In some implementations, the rate at which charge is depleted from the capacitor in the Implanted Neural Stimulator 114 depends on the stimulus parameters, the electrode-tissue load, and the internal circuitry of the stimulator. By virtue of such dependence, the rate of charge depletion from the capacitor can be used to determine the impedance of the electrode-tissue interface. The rate of charge depletion may reveal an RF impedance characteristic of the Rx antenna 238 from which the electrode-tissue impedance can be extracted. For example, if the electrode-tissue impedance is mostly resistive and is sufficiently low (for example, z=300-500Ω), the intended stimulus current will be driven to the targeted tissue, and the charge on the capacitor will deplete at an expected rate. In contrast, if the electrode-tissue impedance has a high-value resistance or is dominated by series-capacitance, the intended stimulus current may not be delivered. An example of high-value resistance is demonstrated in FIG. 4D below. If the programmed stimulus current is not delivered to the tissue, the charge on the capacitor will deplete at a lower rate than expected. In both cases, the rate of charge depletion may revealed the RF impedance characteristic of the Rx antenna, and from this rate a deduction about the impedance of the electrode-tissue interface can be made.

In some implementations, a circuit internal to the Implanted Neural Stimulator 114 may allow connection of the current-driver circuit to a calibrated internal load.

In some implementations, a calibrated internal load in the Implanted Neural Stimulator 114 may be programmed to specific impedance values. In these implementations, the calibrated internal load can be placed anywhere on the Implanted Neural Stimulator 114.

In some implementations, the Implanted Neural Stimulator 114 may drive current into the calibrated internal load while either the current or the load is swept through a range of values, and the corresponding family of unique complex RF reflection coefficients may be captured for reference. Subsequently, when the stimulator is configured to drive current through the electrode-tissue load, which is unknown, the RF reflection coefficient curve may be captured and compared to the family of reference curves. By matching the curve of the unknown electrode-tissue load to the curve of a known load, the electrode-tissue impedance may be deduced.

In some implementations, a circuit internal to the Implanted Neural Stimulator 114 may facilitate a system self-check to ascertain the suitability of the wireless stimulation system 100 to provide stimulation therapy. For example, for a system self-check, the stimulator may drive various currents into an internal load, and for each current level the average RF power is swept while the RF reflection is observed. These measurements may be used for a reference to compare to electrode-tissue load measurements during the self-check.

For purpose of the analysis it may be advantageous to view the change of the measurand (RF reflection, or reverse RF voltage) relative to its initial value, and the change in the independent variable (average RF power) relative to its initial value. For example, for measurand V, the change would be $(V-V_{min})$. Further, it may be advantageous to normalize the data. The data shown in FIG. 4A through 4B was normalized to the reference measurements as follows: The maximum and minimum RF reflections (reverse RF voltages, $V_{max}$ and $V_{min}$) of these reference measurements were extracted, and the difference was used as the normalization factor. For example, the subsequent measurand changes were normalized as follows:

$$v = (V - V_{min})/(V_{max} - V_{min}),$$

where V is the measured reverse RF voltage, and v (lower case) implies normalized. Similarly the independent variable changes were normalized as follows:

$$p = (P - P_{min})/(P_{max} - P_{min}),$$

where P is the average transmitted RF power and p (lower case) implies normalized.

Figure 4A:
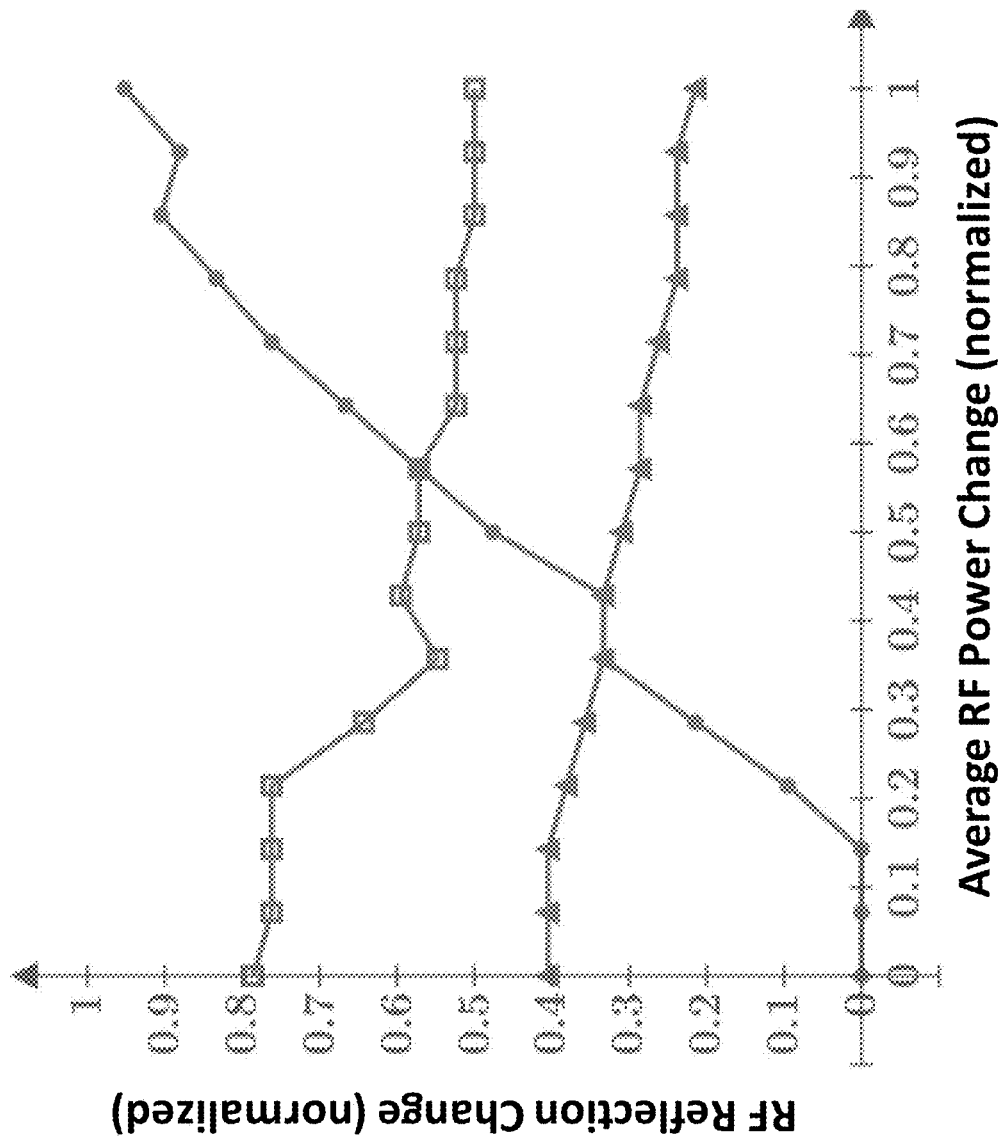
FIGS. 4A-4D illustrate examples of normalized reflection versus normalized power under various loading conditions.

FIG. 4A shows the reference measurements, normalized change in RF reflection versus normalized change in RF average power for three different currents driven into the internal load. The curves show: 1) minimum current through the internal load (circles), 2) medium current through the internal load (triangles), 3) maximum current through the internal load (squares). In some cases, minimum can be around 0.1 mA; medium can be around 6 mA; and maximum can be around 12 mA. In the case of low current, the charge on the capacitor builds steadily higher as the average RF power is increased. This is indicated on the plot (circles) by the rising trajectory of the RF reflection. In the case of medium current, the charge on the capacitor remains relatively flat as the average RF power is increased. This is indicated on the plot (triangles) by the relatively flat trajectory of the RF reflection. For the case of high current, the charge on the capacitor remains relatively flat (but at different level) as the average RF power is increased. This is indicated on the plot (squares) by the relatively flat trajectory (at a higher level) of the RF reflection.

Figure 4B:
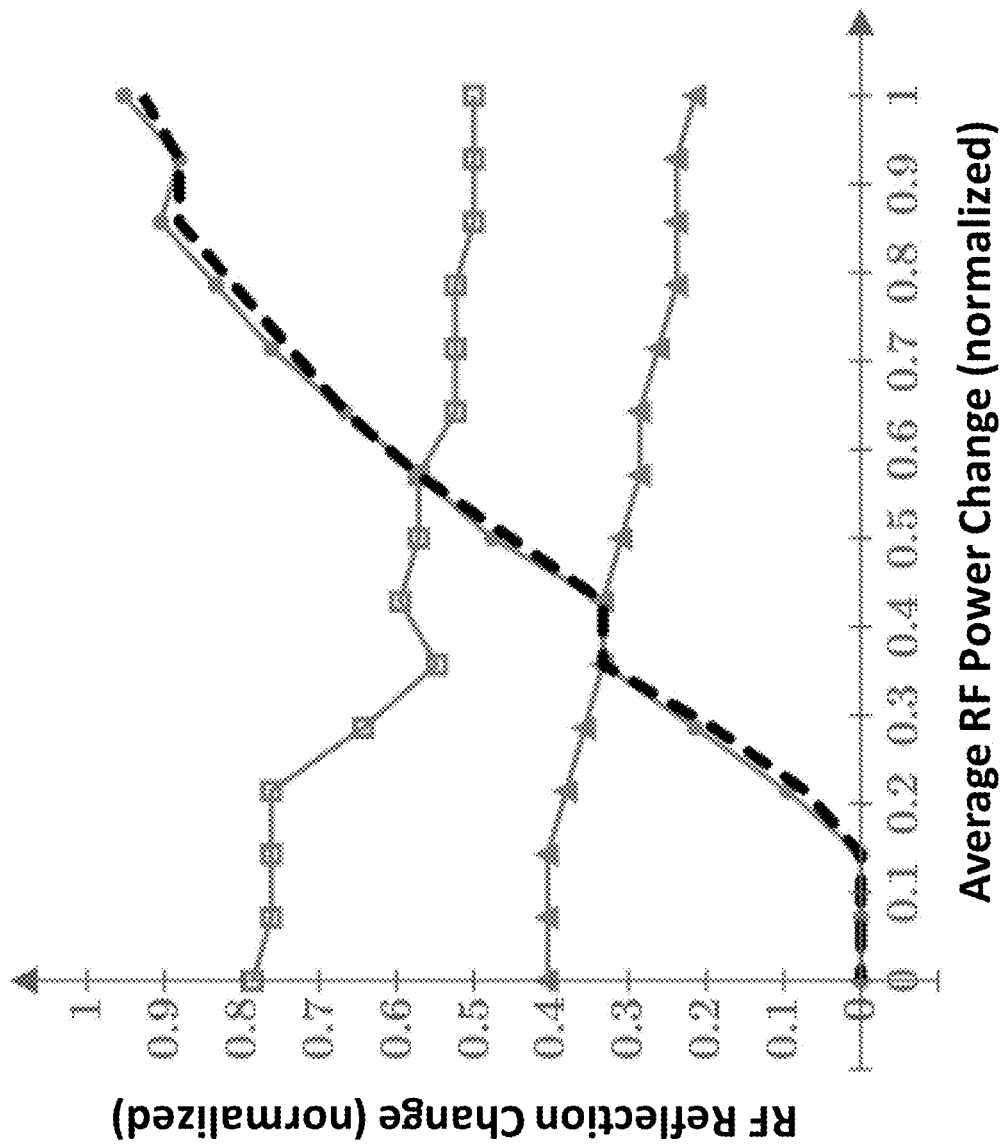

In some implementations, the wireless stimulation system 100 self-check may include various fault checks. For example, when the Implanted Neural Stimulator 114 is energized but not programmed to drive stimulus current, the RF reflection should be similar to that shown for the minimum-current case of FIG. 4A. This is shown in FIG. 4B, where the RF reflection for the un-configured stimulator (dashed line) is overlaid onto the plots of FIG. 4A.

Figure 4C:
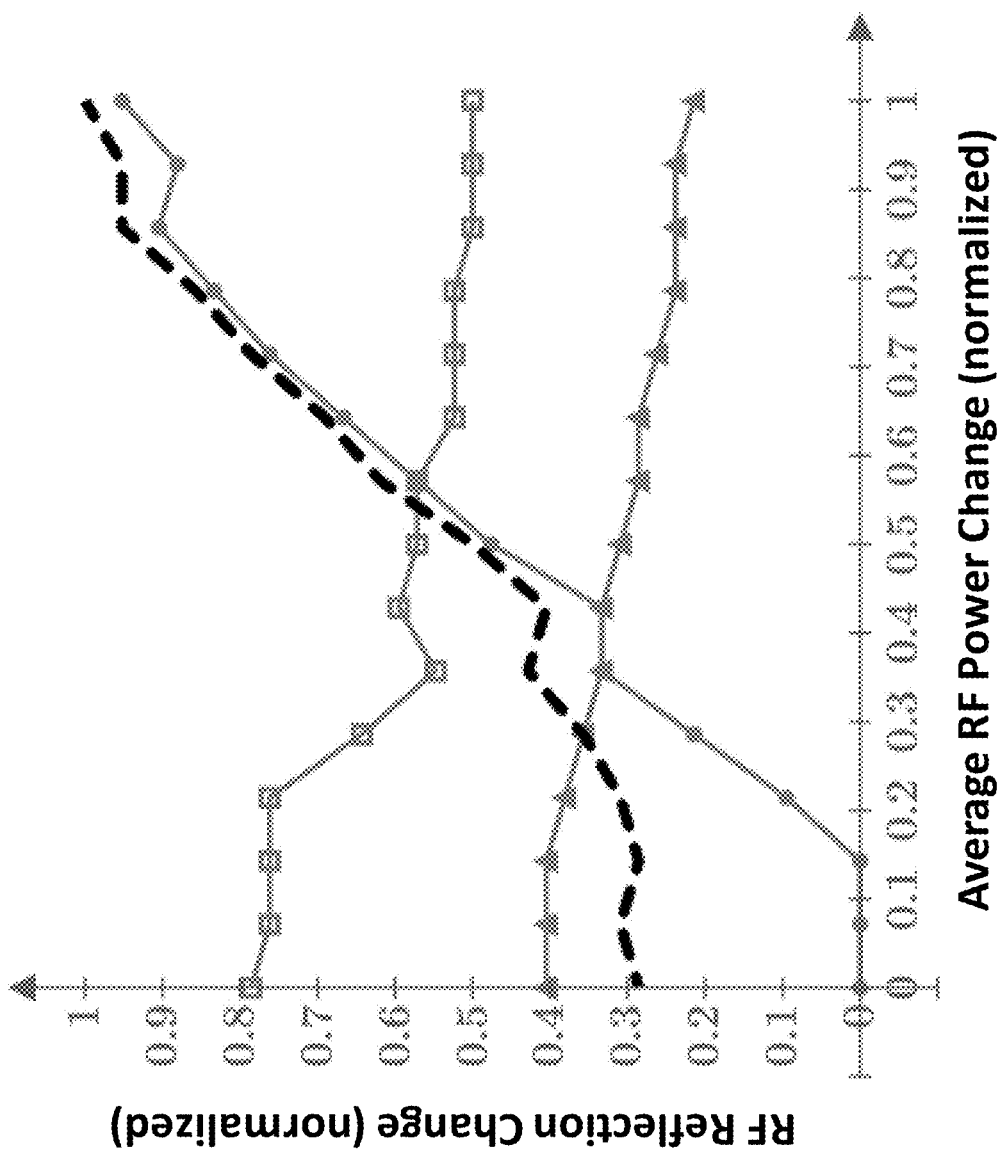

Further, based on the reference measurements shown in FIG. 4A, it is feasible for the system to test for a fault in the stimulus-current driver (such as a broken electrode). For example, the Implanted Neural Stimulator 114 could be programmed to drive stimulus current through selected pairs of electrodes, and the RF reflection for each pair is compared against the reference measurements in FIG. 4A. When the stimulator is programmed to drive a given stimulus current through tissue, the RF reflection should be similar to that of when the same current is driven through the internal load. However, should there be a damaged wire at the electrode, for example, the current through the circuit would be blocked, meaning the RF reflection would resemble the minimum-current curve of FIG. 4A. This case is shown in FIG. 4C, plotted with the reference measurements of FIG. 4A.

Figure 4D:
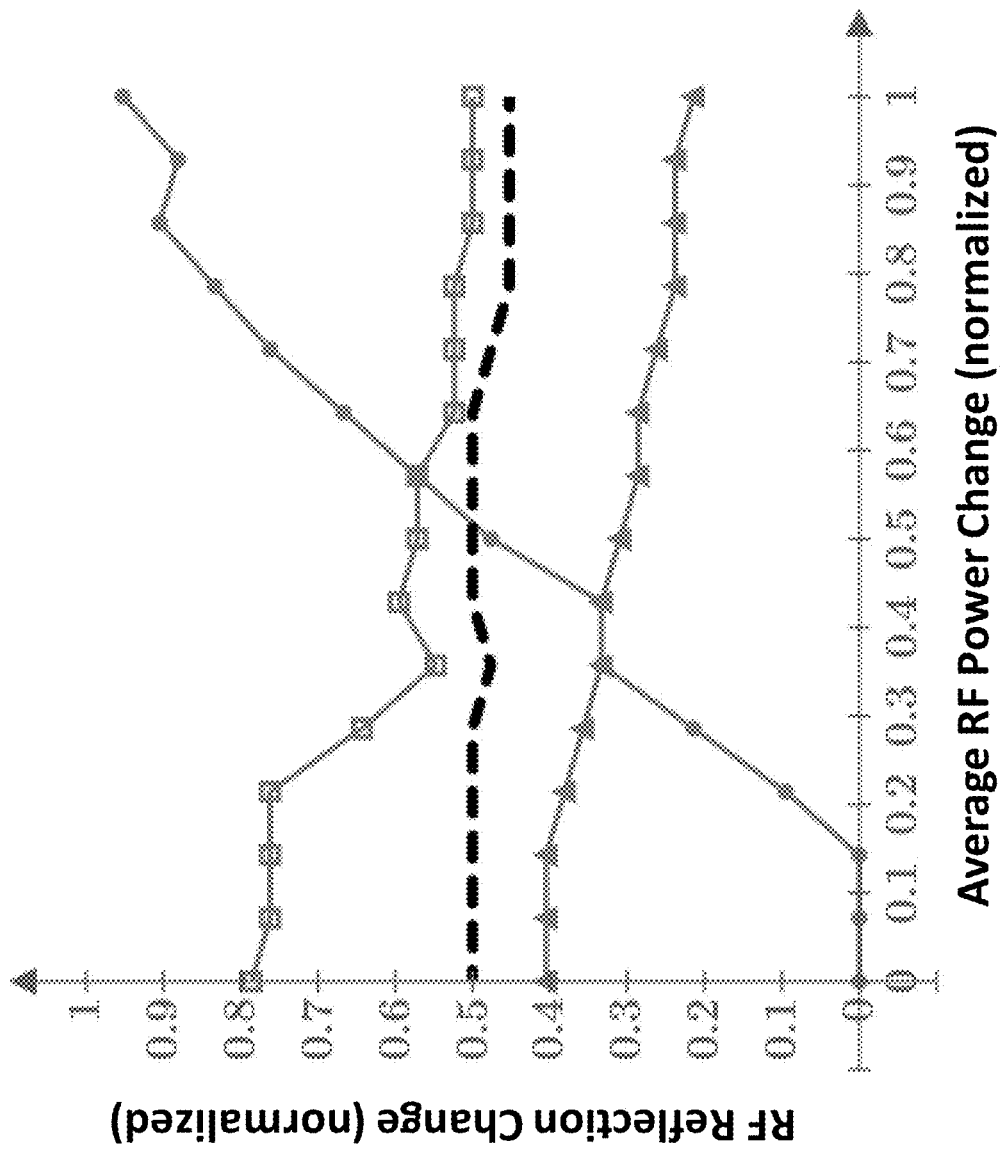

Further, during normal operation, the tissue impedance may be unknown, however, it will likely be within an expected range, and a fault-check could verify this condition. To illustrate, FIG. 4D shows the RF reflection (dashed line) when a 500Ω resistor is connected in series with the electrodes, and a medium current is delivered. The result shows the RF reflection falls within the expected range. However, for example, if the result showed the RF reflection overlaid the low-current curve, a fault would be evident.

By capturing the reflected RF signal and applying the analysis methods described herein, it is possible to measure the impedance at the electrode-tissue interface. Furthermore, by measuring said impedance, the system may adjust stimulus parameters to compensate, thereby maintaining the efficacy of stimulation.

FIG. 5 shows an example of a flow chart 500 for implementing stimulation adjustment on an implantable wireless stimulator device based on sensing of tissue-electrode impedance. As illustrated by step 502, a first set of radio-frequency (RF) pulses are transmitted from an external pulse generator (such as RF pulse generator module 106) to an implantable wireless stimulator device (such as implanted neural stimulator 114) via non-inductive electric radiative coupling. Consistent with discussions from FIGS. 1-3, electric currents are created from the first set of RF pulses and flown through a calibrated internal load on the implantable wireless stimulator device. The calibrated internal load represents a load condition that is pre-determined and imposed on, for example, an electrode on implanted neural stimulator 114.

In response to the electric currents flown through the calibrated internal load, flow chart 500 proceeds to recording, on the external pulse generator, a first set of RF reflection measurements (504). This recording measures, for example, RF signals reflected from the implantable neural stimulator 114 and received by RF pulse generator module 106.

Next, a second set of radio-frequency (RF) pulses are transmitted, from the external pulse generator and via electric radiative coupling, to the implantable wireless stimulator device such that stimulation currents are created from the second set of RF pulses and flown through an electrode of the implantable wireless stimulator device to tissue surrounding the electrode (506). Here, the stimulation currents flow through the stimulator circuitry, the electrode, and the electrode-tissue interface.

In response to the stimulation currents flown through the electrode to the surrounding tissue, a second set of RF reflection measurements is recorded on the external pulse generator (508). This second set of reflection measurements are based on RF signals reflected from the implantable neural stimulator 114 and received by RF pulse generator module 106.

By comparing the second set of RF reflection measurements with the first set of RF reflections measurements, an electrode-tissue impedance is characterized (510). When the electrode-tissue impedance is characterized as resistive, one or more input pulses to be transmitted by the external pulse generator to the implantable wireless stimulator device can be adjusted such that stimulus currents created from these input pulses on the implantable wireless stimulator device are likewise adjusted to compensate for a resistive electrode-tissue impedance. When the electrode-tissue impedance is characterized as capacitive, one or more input pulses to be transmitted by the external pulse generator to the implantable wireless stimulator device can be adjusted such that stimulus currents created from these input pulses on the implantable wireless stimulator device are likewise adjusted to compensate for a capacitive electrode-tissue impedance. Here, the adjustment of input pulses involves maintaining a steady-state delivery of electrical power to the implantable wireless stimulator device such that electrical energy is extracted from the input pulses as fast as electrical energy is consumed to generate the stimulus currents with one or more pulse parameters that have been varied to accommodate the resistive electrode-tissue impedance. Such stimulus currents are delivered from the electrode to the surrounding tissue. Examples of pulse parameters include: a pulse width, a pulse amplitude, and a pulse frequency.

Based on results of characterizing the electrode-tissue impedance, a stimulation session can be automatically chosen. The selection process may include: determining input pulses to be transmitted by the external pulse generator to the implantable wireless stimulator device such that stimulus currents are created on the implantable wireless stimulator device and delivered by the electrode on the implantable wireless stimulator device to the surrounding tissue in a manner that, for example, maintains therapy consistency despite variations in electrode-tissue impedance. In one instance, the second set of radio-frequency (RF) pulses may be updated to obtain updated second set of RF reflection measurements; and then the updated second set of RF reflection measurements may be compared with the first set of RF reflection measurements. In this instance, the updating and comparing steps can be performed iteratively until desired RF reflection measurements are obtained.

The characterizing step may also lead to automatic fault checking according to results from such characterization. In one instance, automatic fault checking includes automatic detecting a damaged wire in a circuit leading to the electrode on the implantable wireless stimulator device, as illustrated in, for example, FIG. 4C.

A number of implementations have been described. Nevertheless, it will be understood that various modifications may be made. Accordingly, other implementations are within the scope of the following claims.

What is claimed is:

1. A method of operating an external pulse generator and an associated implantable wireless stimulator that applies stimulation to surrounding internal tissue, the method comprising:

non-inductively transmitting, from an antenna of the external pulse generator to an antenna of the implantable wireless stimulator, three or more radio-frequency (RF) signals, energy from the radio-frequency (RF) signals being applied to internal tissue adjacent one or more electrodes of the implantable wireless stimulator;

receiving, at the external pulse generator antenna, a reflected RF signal for each of the transmitted RF signals such that three or more reflected RF signals are received, the reflected RF signals resulting from at least a total impedance of the implantable wireless stimulator;

detecting a rate-of-change of power of the reflected RF signals, the rate-of-change of power indicating how power changes from a first of the reflected RF signals to a last of the reflected RF signals; and determining, based on the rate-of-change of power of the reflected RF signals, a sub-impedance of the total impedance, the sub-impedance including only an electrode-tissue impedance at an electrode-tissue interface between the internal tissue and the one or more electrodes of the implantable wireless stimulator.

2. The method of claim 1, further comprising storing, by the implantable wireless stimulator, the energy from the RF signals as charge in one or more capacitors of the implantable wireless stimulator, the charge then being applied to the internal tissue adjacent one or more electrodes of the implantable wireless stimulator, the rate-of-change of power of the reflected RF signals indicating a rate-of-charge depletion of the one or more capacitors as the charge is applied to the internal tissue.

3. The method of claim 1, wherein a power level of each of the RF signals when transmitted is different regardless of a power level of the reflected RF signals.

4. The method of claim 3, wherein the power level of each of the RF signals is increased as compared to a power level of a previously transmitted RF signal.

5. The method of claim 4, wherein the determining the electrode-tissue impedance at the electrode-tissue interface includes comparing the rate-of-change of power of the reflected RF signals to one or more known rates-of-change of power of second reflected RF signals reflected from the implantable wireless stimulator, the second reflected RF signals obtained by transmitting second RF signals with power levels the same as the power levels of the RF signals and a driving circuit, configured to apply the energy to the internal tissue, being configured to be coupled to a known impedance to drive energy through the known impedance and not through the internal tissue when the second RF signals are transmitted.

6. The method of claim 1, further comprising modifying the RF signals to compensate for the electrode-tissue impedance.

7. The method of claim 6, wherein modifying the RF signals comprises modifying one or more of a pulse width, a pulse frequency, and a pulse amplitude.

8. The method of claim 1, wherein the implantable wireless stimulator includes a plurality of electrodes, the method includes repeating the steps of non-inductively transmitting, receiving, detecting, and determining, for each of the electrodes to determine an electrode-tissue impedance for each of the plurality of electrodes.

9. The method of claim 1, wherein determining the sub-impedance includes determining a malfunction of one of the one or more electrodes based on the rate-of-change of power of the reflected RF signals.

10. The method of claim 1, further comprising adjusting a voltage provided to a current driver in the implantable wireless stimulator to compensate for the electrode-tissue impedance.

11. A method of operating an external pulse generator and an associated implantable wireless stimulator that applies stimulation to surrounding internal tissue, the method comprising:
non-inductively transmitting, from an antenna of the external pulse generator to an antenna of the implantable wireless stimulator, three or more radio-frequency (RF) signals;
storing, in one or more capacitors of the implantable wireless stimulator, energy transmitted with the RF signals, energy from which is to be applied to internal tissue adjacent one or more electrodes of the implantable wireless stimulator via a driving circuit of the implantable wireless stimulator;
receiving, at the external pulse generator antenna, a reflected RF signal for each of the transmitted RF signals such that three or more reflected RF signals are received, the reflected RF signals resulting from at least a total impedance of the implantable wireless stimulator, wherein a power level of each of the RF signals when transmitted is increased as compared to a power level of a previously transmitted RF signal regardless of a power level of the reflected RF signals;
determining, using the reflected RF signals, a rate-of-change of power of the reflected RF, the rate-of-change of power indicating how power changes from a first of the reflected RF signals to a last of the reflected RF signals;
comparing the rate-of-change of power of the reflected RF signals to one or more known rates-of-change of power of second reflected RF signals reflected from the implantable wireless stimulator, the second reflected RF signals obtained by transmitting second RF signals with power levels the same as the power levels of the RF signals and the driving circuit of the implantable wireless stimulator being configured to be coupled to a known impedance to drive energy through the known impedance and not through the internal tissue when the second RF signals are transmitted; and
determining, based on the comparison, a sub-impedance of the total impedance, the sub-impedance including only an electrode-tissue impedance at an electrode-tissue interface between the internal tissue and the one or more electrodes of the implantable wireless stimulator.

12. A system comprising:
an implantable wireless stimulator device comprising:
a first antenna;
one or more electrodes; and
one or more capacitors electrically connected to the first antenna and to the one or more electrodes; and
an external pulse generator comprising:
a second antenna configured to:
non-inductively transmit, to the first antenna, three or more radio-frequency (RF) signals, energy from the RF signals being applied to internal tissue adjacent the one or more electrodes, and
receive a reflected RF signal for each of the transmitted RF signals such that three or more reflected RF signals are received, the reflected RF signals resulting from at least a total impedance of the implantable wireless stimulator, wherein a power level of each of the RF signals when transmitted is different regardless of a power level of the reflected RF signals; and circuitry to:
detect a rate-of-change of power of the reflected RF signals, the rate-of-change of power indicating how power changes from a first of the reflected RF signals to a last of the reflected RF signals; and
determine, based on the rate-of-change of power of the reflected RF signals, a sub-impedance of the total impedance, the sub-impedance including only an electrode-tissue impedance at an electrode-tissue interface between the internal tissue and the one or more electrodes of the implantable wireless stimulator.

13. The system of claim 12, wherein the one or more capacitors stores energy transmitted with the one or more RF signals, the rate-of-change of power of the reflected RF signals indicating a rate-of-charge depletion of the one or more capacitors as a charge from the one or more capacitors is applied to the internal tissue.

14. The system of claim 13, further comprising transmitting the RF signals to maintain a particular voltage of the one or more capacitors.

15. The system of claim 12, wherein a power level of each of the RF signals when transmitted is increased as compared to a power level of a previously transmitted RF signal.

16. The system of claim 12, wherein the determine the electrode-tissue impedance at the electrode-tissue interface includes comparing the rate-of-change of power of the reflected RF signals to one or more known rates-of-change of power of second reflected RF signals reflected from the implantable wireless stimulator, the second reflected RF signals obtained by transmitting second RF signals at same power levels as the power levels of the RF signals and a driving circuit, configured to apply the energy to the internal tissue, being configured to be coupled to a known impedance to drive energy through the known impedance and not through the internal tissue when the second RF signals are transmitted.

17. The system of claim 16, wherein the implantable wireless stimulator device includes a plurality of electrodes and the electrode-tissue impedance is determined for one electrode, and the second antenna is further configured to transmit a plurality of third RF signals to determine an electrode-tissue impedance of another of the plurality of electrodes.

18. The system of claim 12, wherein the circuitry automatically modifies the RF signals to compensate for the electrode-tissue impedance.

19. The system of claim 12, wherein the implantable wireless stimulator device further comprises a current driver electrically connected to the one or more capacitors and electrodes, wherein a voltage provided to the current driver is adjusted to compensate for the electrode-tissue impedance.

20. The method of claim 11, wherein comparing the rate-of-change of power of the reflected RF signals to the one or more known rates-of-change of power of the second reflected RF signals includes comparing the rate-of-change of power of the reflected RF signals to a plurality of rates-of-change of power of the second reflected RF signals, each of the plurality of rates-of-change of power is determined using a different subset of the second reflected RF signals and using a different known impedance such that each the plurality of rates-of-change of power are determined using a different known impedance coupled to the driving circuit of the implantable wireless stimulator.

* * * * *